(12) United States Patent
Chen et al.

(10) Patent No.: US 7,279,175 B2
(45) Date of Patent: Oct. 9, 2007

(54) STENT COATED WITH A SUSTAINED-RELEASE DRUG DELIVERY AND METHOD FOR USE THEREOF

(75) Inventors: Jianbing Chen, Belmont, MA (US); Paul Ashton, Boston, MA (US)

(73) Assignee: Psivida Inc., Watertown, MA (US)

( * ) Notice: Subject to any disclaimer, the term of this patent is extended or adjusted under 35 U.S.C. 154(b) by 567 days.

(21) Appl. No.: 10/245,840

(22) Filed: Sep. 17, 2002

(65) Prior Publication Data
US 2003/0108588 A1    Jun. 12, 2003

Related U.S. Application Data

(60) Provisional application No. 60/322,428, filed on Sep. 17, 2001, provisional application No. 60/372,761, filed on Apr. 15, 2002.

(51) Int. Cl.
*A61F 2/02* (2006.01)
*A61F 2/06* (2006.01)

(52) U.S. Cl. ............... 424/423; 623/1.42; 424/426

(58) Field of Classification Search ......... 424/422, 424/423, 426; 514/255, 597; 623/1.42
See application file for complete search history.

(56) References Cited

U.S. PATENT DOCUMENTS

| | | | |
|---|---|---|---|
| 4,650,803 A * | 3/1987 | Stella et al. ............ | 514/291 |
| 5,464,650 A * | 11/1995 | Berg et al. ............ | 427/2.3 |
| 5,624,411 A | 4/1997 | Tuch | |
| 5,972,027 A | 10/1999 | Johnson | |
| 6,051,576 A | 4/2000 | Grazyna | |
| 6,639,014 B2 * | 10/2003 | Pathak et al. .......... | 525/90 |
| 2003/0118528 A1 * | 6/2003 | Walters et al. ........ | 424/59 |

FOREIGN PATENT DOCUMENTS

| | | | |
|---|---|---|---|
| EP | 0 623 354 | | 11/1994 |
| EP | WO95/20567 | * | 8/1995 |
| WO | WO91/12779 | | 9/1991 |
| WO | WO93/06792 | | 4/1993 |
| WO | WO96/32907 | | 10/1996 |
| WO | WO 02/087586 | | 11/2002 |

OTHER PUBLICATIONS

Ingrams D. R.: "Slow-Release 5-Fluorouracil and Triamcinolone Reduces Subglottic Stenosis in a Rabbit Model" Annals of Otology, Rhinology and Laryngology, Annals Publ., St. Louis, MO, US; vol. 109, No. 4, Apr. 2000, pp. 422-424.

(Continued)

*Primary Examiner*—Sharon E. Kennedy
(74) *Attorney, Agent, or Firm*—Fish & Neave IP Group Ropes & Gray LLP

(57) ABSTRACT

An intraluminal medical device comprises a stent having a coating applied to at least part of an interior surface, an exterior surface, or both. The coating comprises a sustained release formulation of a combination of pharmaceutical compounds dispersed within a biologically tolerated polymer composition. The choice of the combination of pharmaceutical compounds are intended to reduce neointimal hyperplasia restenosis.

38 Claims, 9 Drawing Sheets

OTHER PUBLICATIONS

Lin et al.: "(o-and p-Nitrobenzyloxycarbonyl)-5-fluorouracil Derivatives as Potential Conjugated Bioreductive Alkylating Agents" Journal of Medicinal Chemistry, American Chemical Society, Washington, US, vol. 29, No. 1, 1986, pp. 84-89.

Double et al: "Nucleoside analogues. 5. Molecular combination of anti-cancer drugs: activity of 5-fluorouracil/nitrosourea combination against mouse colon tumours" Anti-Cancer Drug Design, Basingstroke, GB, vol. 1, No. 2, 1986, pp. 133-139-140.

* cited by examiner

STENT COATED WITH A SUSTAINED-RELEASE DRUG DELIVERY AND METHOD FOR USE THEREOF

CROSS-REFERENCE TO RELATED APPLICATIONS

This application claims the benefit of U.S. Provisional Application Nos. 60/322,428, filed Sep. 17, 2001 and 60/372,761, filed Apr. 15, 2002, the specifications of each of which are hereby incorporated by reference in their entirety.

FIELD OF THE INVENTION

The present invention generally relates to an improved intraluminal medical device and to a method for treating tissues. More particularly, the present invention relates to a stent coated with a sustained-release drug delivery system for supporting and reinforcing an enlarged vessel, the system having a therapeutically beneficial advantage of reducing the incidence, recurrence, or both, of restenosis.

BACKGROUND OF THE INVENTION

A stent is a generally longitudinal tubular device formed of biocompatible material, preferably a metallic or plastic material. Stents are useful in the treatment of stenosis, strictures or aneurysms in body vessels, such as blood vessels. It is well-known to employ a stent for the treatment of diseases of various body vessels. The device is implanted either as a "permanent stent" within the vessel to reinforce collapsing, partially occluded, weakened or abnormally dilated sections of the vessel or as a "temporary stent" for providing therapeutic treatment to the diseased vessel. Stents are typically employed after angioplasty of a blood vessel to prevent restenosis of the diseased vessel. Stents may be useful in other body vessels, such as the urinary tract and the bile duct.

A typical stent includes an open flexible configuration. The stent configuration allows the stent to be configured in a radially compressed state for intraluminal catheter insertion into an appropriate site. Once properly positioned within the lumen of a damaged vessel, the stent is radially expanded to support and reinforce the vessel. Radial expansion of the stent may be accomplished by an inflatable balloon attached to the catheter, or the stent may be of the self-expanding type that will radially expand once deployed. An example of a suitable stent is disclosed in U.S. Pat. No. 4,733,665, which is incorporated herein by reference in its entirety.

Stents find various uses in surgical procedures. For instance, stents are widely used in angioplasty. Angioplasty involves insertion of a balloon-tipped catheter into an artery at the site of a partially obstructive atherosclerotic lesion. Inflation of the balloon can rupture the intima and media, dramatically dilating the vessel and relieving the obstruction. About 20 to 30% of obstructions reocclude in a few days or weeks, but most can be redilated successfully. Use of stents significantly reduces the reocclusion rate. Repeat angiography one year after angioplasty reveals an apparently normal lumen in about 30% of vessels on which the procedure has been performed.

Angioplasty is an alternative to bypass surgery in a patient with suitable anatomic lesions. The risk is comparable with that of surgery. Mortality is 1 to 3%; myocardial infarction rate is 3 to 5%; emergency bypass for intimal dissection with recurrent obstruction is required in <3%; and the initial success rate is 85 to 93% in experienced hands.

Stents are also used in percutaneous endovascular therapy. Many new treatments for vascular disease (occlusions and aneurysms) avoid open surgery. These treatments may be performed by interventional radiologists, vascular surgeons, or cardiologists. The primary approach is percutaneous translumninal angioplasty (PTA), whereby a small high-pressure balloon is used to open an obstructed vessel. However, because of the high recurrence rate of obstruction, alternative methods may be necessary.

A stent, such as a metallic mesh-like tube, is generally inserted into a vessel at an obstructed site. As stents can be very strong, they tend to keep vessels open much better than balloons alone. Moreover, the recurrence rate of obstruction is reportedly lower when stents are used. Stents work well in larger arteries with high flow, such as iliac and renal vessels. They work less well in smaller arteries, and in vessels in which the occlusions are long. Stents for carotid disease are being studied.

There are at least two known causes of post-operative restenosis—elastic recoil, wherein the vessel contracts due to the natural elasticity of the vessel walls, and neointimal hyperplasia, wherein medial cells proliferate in response to immune system triggers. Stents have proven useful in reducing the incidence and/or severity of post-operative elastic recoil restenosis, as they resist the tendency of blood vessels to restenose after removal of the balloon. Stents have proven less useful for treatment of neointimal hyperplasia, which arises out of a complex immune response to expanding and fracturing the atherosclerotic plaque. In the case of neointimal hyperplasia, the initial expansion and fracture of the atherosclerotic lesion initiates inflammation, which gives rise to a complex cascade of cellular events that activates the immune system, which in turn gives rise to the release of cytokines that stimulate cell multiplication in the smooth muscle layers of the vessel media. This cell stimulation eventually causes the vessel to restenose.

Various approaches to the problem of neointimal hyperplasia have been attempted. Among these approaches are: subsequent stent placement, debulking, repeat angioplasty, and laser treatment. Another recent approach has been to coat the stent with an immunosuppressant or a chemotherapeutic drug. Immunosuppressant drugs, such as rapamycin, target cells in the G1 phase, preventing initiation of DNA synthesis. Chemotherapeutic drugs, such as paclitaxel (Taxol—Bristol-Myers Squibb) and other taxane derivatives, act on cells in the M phase, by preventing deconstruction of microtubules, thereby interrupting cell division. While these approaches present some promise, they also suffer certain limitations, such as the tendency for rapamycin and taxanes to quickly disperse from the stent site, thereby both limiting the drugs' effective duration in proximity to the stent and also risking undesirable systemic toxic effects.

There is therefor a need for an improved stent that will provide sustained-release of pharmaceutically active compounds, such as immunosuppressant, antiproliferative, chemotherapeutic, and anti-inflammatory drugs, at or near the site of stent implantation that alleviates or avoids the problem of rapid depletion of drug from the stent site. There is also a need for an improved drug that may be employed in such a stent.

There is furthermore a need for an improved stent that will provide sustained-release of pharmaceutically active compounds, such as immunosuppressant, chemotherapeutic, and anti-inflammatory drugs, at or near the site of stent implantation that does not suffer the drawbacks of causing systemic toxic effects of the immunosuppressant, chemotherapeutic, and anti-inflammatory drugs. There is also a need for an improved drug that may be employed in such a stent.

SUMMARY OF THE INVENTION

The foregoing and other needs are provided by embodiments according to the present invention, which provide a sustained-release drug delivery system.

In certain embodiments, the system comprises: two or more pharmaceutical agents (a "drug combination") dissolved or dispersed in a biologically tolerated polymer to form a coating on a medical device in which sustained release of the pharmaceutical agents occurs, e.g., for at least a few days, and preferably for more than 15, 30, 45 or even 60 days. In preferred embodiments, the pharmaceutical agents are provided in low-solubility form, such as in the form of a homo- or hetero-codrug, as a prodrug, through the use of particular salts, as a lyophilate from an organic solvent, etc. In other embodiments, the drugs are rendered in sustained release form by virtue of their mixture with the polymer for forming the coating. The sustained release may achieve the release in a number of different ways: a) constant release with time, (b) release rate diminishing with time, c) burst release, and d) pulsed release where all of the active material is released suddenly at a certain time. The skilled artisan would readily appreciate that such sustained release formulations may be designed by regulating the rate of dissolution, the rate of permeability, or the swelling rates, which in turn may be controlled by controlling the pH, moisture and temperature of the environment, and chemical properties of the polymeric matrix, such as for example its size, shape and thickness.

For example, in certain embodiments, the polymer matrix may be comprised of a semi-permeable membrane with pores of sufficient size to allow for the selective release of the pharmaceutical agents. In such cases, the matrix may be rendered more permeable to agents of a smaller molecular weight. This system may be particularly suitable where the pharmaceutical agent has high solubility in the physiological fluid.

An example of such a system includes a medical device comprising a substrate having a surface and a pharmaceutically active agent dispersed adjacent to said surface, wherein said pharmaceutically active agent comprises at least two moieties mixed, dispersed, or bonded together, said at least two moieties comprising A and B with A having a molecular weight greater than B; and a polymer matrix encapsulating said pharmaceutically active agent; said matrix further comprises a semi-permeable lattice having intermittent pores with cross sectional area sufficient to restrict the passage of moiety A but to allow the passage of moiety B. In yet another embodiment, the system includes a medical device comprising a substrate having a surface and a pharmaceutically active agent dispersed adjacent to said surface, wherein said pharmaceutically active agent comprises at least two moieties mixed, dispersed, or bonded together, said at least two moieties comprising A and B wherein A has a solubility that is at least 50 times, 25 times, 20 times, 15 times, 10 times, 5 times, 2 times more than the solubility of B in physiological solvents.

In yet another embodiment, the system comprises a single pharmaceutical agent dissolved or dispersed in a biologically tolerated polymer o form a coating on a medical device in which sustained release of the pharmaceutical agent occurs, e.g., for at least a few days, and preferably for more than 15, 30, 45 or even 60 days. In preferred embodiments, the sustained release profile of the pharmaceutical agent is modulated so as to provide sustained release of the pharmaceutical agent over a period of days such as for example., over a period of a few days, and preferably for more than 15, 30, 45 or even 60 days Examples of such pharmaceutical agents include within their scope without limitation the drug can be an anticoagulant, such as an anti-inflammatory agents, anti-neoplastic agents, heparin, antithrombin compounds, platelet receptor antagonists, anti-thrombin antibodies, anti-platelet receptor antibodies, aspirin, protaglandin inhibitors, platelet inhibitors, or tick anti-platelet peptide. The pharmaceutical agent can also be a promoter of vascular cell growth, such as a growth factor receptor antagonists, transcriptional activator or translational promoter. Alternatively, the pharmaceutical agent can be an inhibitor of vascular cell growth, such as a growth factor inhibitor, growth factor receptor antagonists, transcriptional repressor or translational repressor, antisense DNA, antisense RNA, replication inhibitor, inhibitory antibodies, antibodies directed against growth factors, and bifunctional molecules. The pharmaceutical agent can also be a cholesterol-lowering agent, a vasodilating agent, and agents which interfere with endogenous vasoactive mechanisms. Other examples of drugs can include, anti-platelet or fibrinolytic agents, anti-allergic agents, anti-rejection agents, anti-microbial or anti-bacterial or anti-viral agents, hormones, vasoactive substances, anti-invasive factors, anti-cancer agents, antibodies and lymphokines, anti-angiogenic agents, radioactive agents and gene therapy agents, among others. The pharmaceutical agents may be loaded as in its/their original commercial form, or together with polymer or protein carriers, as described herein to achieve delayed and/or consistent release.

In a preferred embodiment, the pharmaceutical agent may be an anti-neoplastic agent such as for example 5-fluorouracil, and its rate of release from the device may be varied as described herein, i.e. by regulating the rate of dissolution, the rate of permeability, or the swelling rates, which in turn may be controlled by controlling the pH, moisture and temperature of the environment, and chemical properties of the polymeric matrix, such as for example its size, shape and thickness. In another embodiment, the 5-fluorouracil may be mixed, dispersed or bonded to another chemical moiety that may reduce its solubility. It yet other embodiments, the 5-fluorouracil may be diffused as a function of the size of the polymeric matrix pores. The matrix diffusion embodiment thus facilitates the delivery by coated device of single drug that ordinarily have high solubility in physiological fluids.

Where the drug combination is provided in the form of a co-drug, certain preferred embodiments of the coating will result in a ratio of eluted active monomers to co-drug of greater than 10:1 (e.g., less than 10 percent co-drug eluting from coating) and even more preferably greater than 20:1, 50:1 or even 100:1.

In certain embodiments, the subject medical device is an intraluminal medical device, e.g., a stent, comprising: a coating comprising a biologically tolerated polymer and a low-solubility pharmaceutical agent dissolved or dispersed in the polymer; and a stent, said stent having an interior surface and an exterior surface; said stent having said coating applied to at least a part of the interior surface, the exterior surface, or both.

While exemplary embodiments of the invention will be described with respect to the treatment of restenosis and related complications following percutaneous transluminal coronary angioplasty, it is important to note that the local delivery of drug/drug combinations may be utilized to treat a wide variety of conditions utilizing any number of medical devices, or to enhance the function and/or life of the device. For example, intraocular lenses, placed to restore vision after cataract surgery is often compromised by the formation of a secondary cataract. The latter is often a result of cellular overgrowth on the lens surface and can be potentially minimized by combining a drug or drugs with the device. Other medical devices which often fail due to tissue ingrowth or accumulation of proteinaceous material in, on and around the device, such as shunts for hydrocephalus, dialysis grafts, colostomy bag attachment devices, ear drainage tubes, leads for pace makers and implantable defibrillators can also benefit from the device-drug combination approach.

Devices which serve to improve the structure and function of tissue or organ may also show benefits when combined with the appropriate agent or agents. For example, improved osteointegration of orthopedic devices to enhance stabilization of the implanted device could potentially be achieved by combining it with agents such as bone morphogenic protein. Similarly other surgical devices, sutures, staples, anastomosis devices, vertebral disks, bone pins, suture anchors, hemostatic barriers, clamps, screws, plates, clips, vascular implants, tissue adhesives and sealants, tissue scaffolds, various types of dressings, bone substitutes, intraluminal devices, and vascular supports could also provide enhanced patient benefit using this drug-device combination approach. Essentially, any type of medical device may be coated in some fashion with a drug or drug combination which enhances treatment over use of the singular use of the device or pharmaceutical agent.

Yet another aspect of the invention provides a method for treating an intraluminal tissue of a patient, the method comprising the steps of: (a) providing a stent having an interior surface and an exterior surface, said stent having a coating on at least a part of the interior surface, the exterior surface, or both; said coating comprising a low-solubility pharmaceutical agent dissolved or dispersed in a biologically-tolerated polymer; (b) positioning the stent at an appropriate intraluminal tissue site; and (c) deploying the stent. In such embosiments, the drug combinations and delivery devices of the present invention may be utilized to effectively prevent and treat vascular disease, and in particular, vascular disease caused by injury.

The subject devices can be used to deliver such pharmaceutical agents as: antiproliferative/antimitotic agents including natural products such as vinca alkaloids (i.e. vinblastine, vincristine, and vinorelbine), paclitaxel, epipidopodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine (cladribine)); platinum coordination complexes (cisplatin, carboplatin), procarbazine, hydroxyurea, mitotane, aminoglutethimide; hormones (i.e., estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); antiinflammatory: such as adrenocortical steroids (cortisol, cortisone, fludrocortisone, prednisone, prednisolone, 6U-methylprednisolone, triamcinolone, betamethasone, and dexamethasone), non-steroidal agents (salicylic acid derivatives, i.e., aspirin; para-aminophenol derivatives, i.e., acetominophen; indole and indene acetic acids (indomethacin, sulindaC7 and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blocker; nitric oxide donors; anti-sense oligionucleotides and combinations thereof; cell cycle inhibitors, mTOR inhibitors, and growth factor signal transduction kinase inhibitors.

Additional advantages of the present invention will become readily apparent to those skilled in the art from the following detailed description, and the appended drawings wherein only a preferred embodiment of the invention is shown and described by way of illustration of the best mode contemplated for carrying out the invention. As will be realized, the present invention is capable of other and different embodiments, and its several details are capable of modifications in various respects, all without departing from the scope of the present invention. Accordingly, the drawings and description are to be regarded as illustrative in nature, and not as restrictive.

BRIEF DESCRIPTION OF THE DRAWINGS

The following description of the embodiment of the present invention can be better understood when read in conjunction with the following drawings, in which like reference numerals are employed throughout to designate similar features, wherein.

Figure 1:
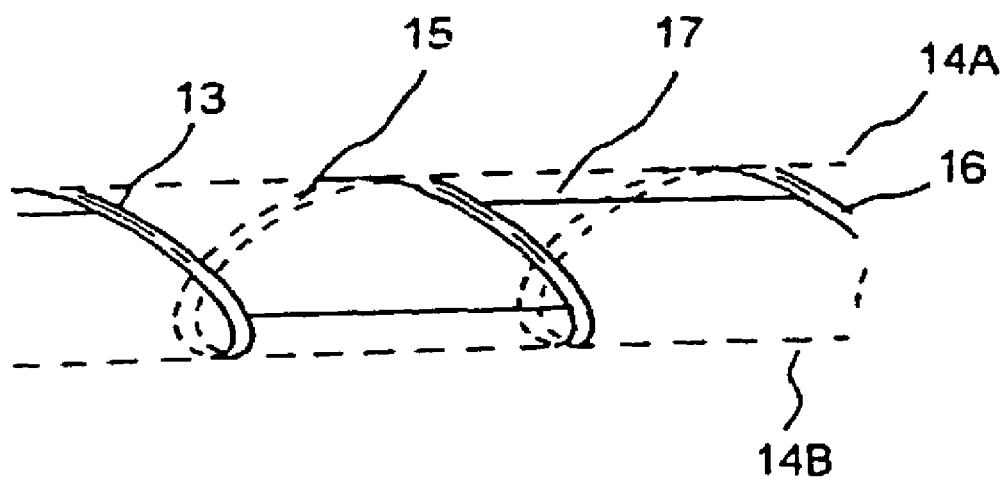
FIG. 1 is a side plan view of a non-deployed stent according to the present invention.

Group C: no plasma treatment, with gamma irradiation.
Group D: with plasma treatment, no gamma irradiation.
Group F: no plasma, no gamma irradiation.

DETAILED DESCRIPTION OF THE INVENTION

In certain embodiments, the present invention provides an intraluminal medical device for implantation into a lumen of a blood vessel, in particular adjacent an intraluminal lesion such as an atherosclerotic lesion, for maintaining patency of the vessel. In particular the present invention provides an elongate radially expandable tubular stent having an interior luminal surface and an opposite exterior surface extending along a longitudinal stent axis, the stent having a coating on at least a portion of the interior or exterior surface thereof. The local delivery of drug combinations from a stent has the following advantages; namely, the prevention of vessel recoil and remodeling through the scaffolding action of the stent and the prevention of multiple components of neointimal hyperplasia or restenosis as well as a reduction in inflammation and thrombosis. This local administration of drugs to stented coronary arteries may also have additional therapeutic benefit. For example, higher tissue concentrations of the drugs may be achieved utilizing local delivery, rather than systemic administration. In addition, reduced systemic toxicity may be achieved utilizing local delivery rather than systemic administration while maintaining higher tissue concentrations. Also in utilizing local delivery from a stent rather than systemic administration, a single procedure may suffice with better patient compliance. An additional benefit of combination drug therapy may be to reduce the dose of each of the therapeutic drugs, agents or compounds, thereby limiting their toxicity, while still achieving a reduction in restenosis, inflammation and thrombosis. Local stent-based therapy is therefore a means of improving the therapeutic ratio (efficacy/toxicity) of anti-restenosis, anti-inflammatory, anti-thrombotic drugs, agents or compounds.

There are a multiplicity of different stents that may be utilized following percutaneous transluminal coronary angioplasty. Although any number of stents may be utilized in accordance with the present invention, for simplicity, a limited number of stents will be described in exemplary embodiments of the present invention. The skilled artisan will recognize that any number of stents may be utilized in connection with the present invention. In addition, as stated above, other medical devices may be utilized.

A stent is commonly used as a tubular structure left inside the lumen of a duct to relieve an obstruction. Commonly, stents are inserted into the lumen in a non-expanded form and are then expanded autonomously, or with the aid of a second device in situ. A typical method of expansion occurs through the use of a catheter-mounted angioplasty balloon which is inflated within the stenosed vessel or body passageway in order to shear and disrupt the obstructions associated with the wall components of the vessel and to obtain an enlarged lumen.

The stents of the present invention may be fabricated utilizing any number of methods. For example, the stent may be fabricated from a hollow or formed stainless steel tube that may be machined using lasers, electric discharge milling, chemical etching or other means. The stent is inserted into the body and placed at the desired site in an unexpanded form. In one exemplary embodiment, expansion may be effected in a blood vessel by a balloon catheter, where the final diameter of the stent is a function of the diameter of the balloon catheter used.

It should be appreciated that a stent in accordance with the present invention may be embodied in a shape-memory material, including, for example, an appropriate alloy of nickel and titanium or stainless steel.

Structures formed from stainless steel may be made self-expanding by configuring the stainless steel in a predetermined manner, for example, by twisting it into a braided configuration. In this embodiment after the stent has been formed it may be compressed so as to occupy a space sufficiently small as to permit its insertion in a blood vessel or other tissue by insertion means, wherein the insertion means include a suitable catheter, or flexible rod.

On emerging from the catheter, the stent may be configured to expand into the desired configuration where the expansion is automatic or triggered by a change in pressure, temperature or electrical stimulation.

Regardless of the design of the stent, it is preferable to have the drug combination dosage applied with enough specificity and a sufficient concentration to provide an effective dosage in the lesion area. In this regard, the "reservoir size" in the coating is preferably sized to adequately apply the drug combination dosage at the desired location and in the desired amount.

In an alternate exemplary embodiment, the entire inner and outer surface of the stent may be coated with drug/drug combinations in therapeutic dosage amounts. It is, however, important to note that the coating techniques may vary depending on the drug combinations. Also, the coating techniques may vary depending on the material comprising the stent or other intraluminal medical device.

Figure 2:
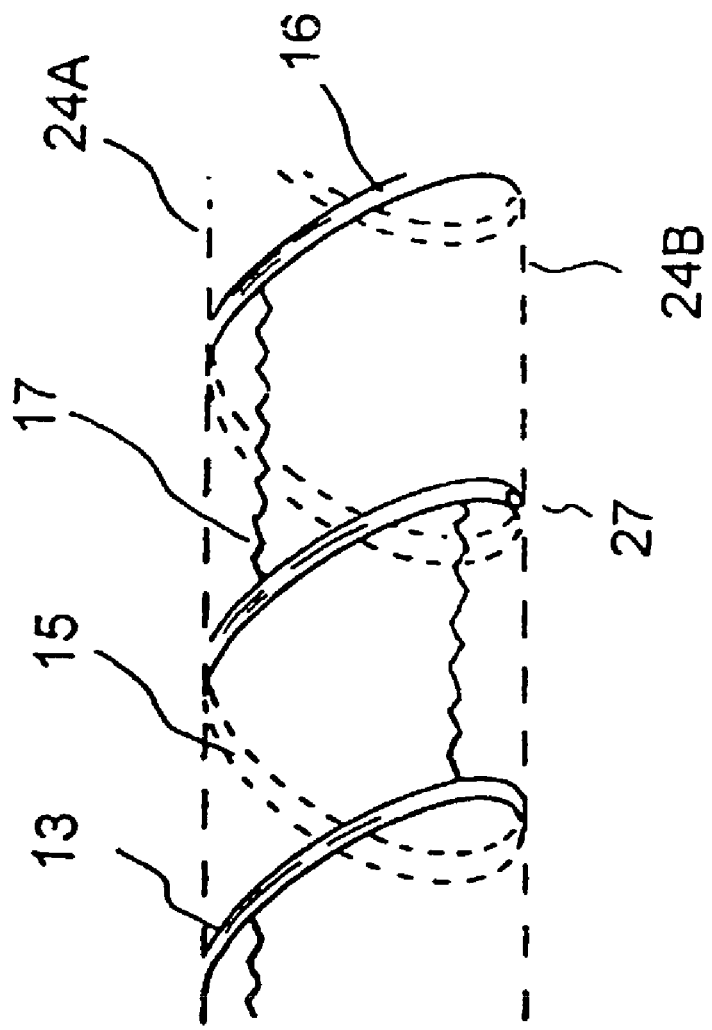
FIG. 2 is a side plan view of a deployed stent according to the present invention.

An embodiment of an intraluminal device (stent) according to the present invention is depicted in FIGS. 1 and 2.

FIG. 1 shows a side plan view of a preferred elongate radially expandable tubular stent 13 having a surface coated with a sustained release drug delivery system in a non-deployed state. As shown in FIG. 1, the stent 13 has its radially outer boundaries 14A, 14B at a non-deployed state. The interior luminal surface 15, the exterior surface 16, or an entire surface of the stent 13 may be coated with a sustained release drug delivery system or comprise a sustained release drug delivery system. The interior luminal surface 15 is to contact a body fluid, such as blood in a vascular stenting procedure, while the exterior surface 16 is to contact tissue when the stent 13 is deployed to support and enlarge the biological vessel or duct.

In an alternate embodiment, an optional reinforcing wire 17 that connects two or more of the adjacent members or loops of the stent structure 13 is used to lock-in and/or maintain the stent at its expanded state when a stent is deployed. This reinforcing wire 17 may be made of a Nitinol or other high-strength material. A Nitinol device is well known to have a preshape and a transition temperature for said Nitinol device to revert to its preshape. One method for treating an intraluminal tissue of a patient using a surface coated stent 13 of the present invention comprises collapsing the radially expandable tubular stent and retracting the collapsed stent from a body of a patient. The operation for collapsing a radially expandable tubular stent may be accomplished by elevating the temperature so that the reinforcing wire 17 is reversed to its straightened state or other appropriate state to cause the stent 13 to collapse for removing said stent from the body of a patient.

FIG. 2 shows an overall view of an elongate radially expandable tubular stent 13 having a sustained release drug delivery system coated stent surface at a deployed state. As shown in FIG. 2, the stent 13 has its radially outer boundaries 24A, 24B at a deployed state. The interior luminal surface 14, the exterior surface 16, or an entire surface of the stent 13 may be coated or may comprise the sustained release drug delivery system. The interior luminal surface 15 is to contact a body fluid, such as blood in a vascular stenting procedure, while the exterior surface 16 is to contact tissue when the stent 13 is deployed to support and enlarge the biological vessel. The reinforcing wire 17 may be used to maintain the expanded stent at its expanded state as a permanent stent or as a temporary stent. In the case of the surface coated stent 13 functioning as a temporary stent, the reinforcing wire 17 may have the capability to cause collapsing of the expanded stent.

The deployment of a stent can be accomplished by a balloon on a delivery catheter or by self-expanding after a pre-stressed stent is released from a delivery catheter. Delivery catheters and methods for deployment of stents are well known to one who is skilled in the art. The expandable stent 13 may be a self-expandable stent, a balloon-expandable stent, or an expandable-retractable stent. The expandable stent may be made of memory coil, mesh material, and the like.

The intraluminal medical device comprises the sustained release drug delivery coating. The inventive stent coating may be applied to the stent via a conventional coating process, such as impregnating coating, spray coating and dip coating.

In one embodiment, an intraluminal medical device comprises an elongate radially expandable tubular stent having an interior luminal surface and an opposite exterior surface extending along a longitudinal stent axis. The stent may include a permanent implantable stent, an implantable grafted stent, or a temporary stent, wherein the temporary stent is defined as a stent that is expandable inside a vessel and is thereafter retractable from the vessel. The stent configuration may comprise a coil stent, a memory coil stent, a Nitinol stent, a mesh stent, a scaffold stent, a sleeve stent, a permeable stent, a stent having a temperature sensor, a porous stent, and the like. The stent may be deployed according to conventional methodology, such as by an inflatable balloon catheter, by a self-deployment mechanism (after release from a catheter), or by other appropriate means. The elongate radially expandable tubular stent may be a grafted stent, wherein the grafted stent is a composite device having a stent inside or outside of a graft. The graft may be a vascular graft, such as an ePTFE graft, a biological graft, or a woven graft. As appropriate, the subject drugs (in monomeric or co-drug form) may be incorporated into the grafted material.

The drug combinations may be incorporated onto or affixed to the stent in a number of ways. In the exemplary embodiment, the drug combination is directly incorporated into a polymeric matrix and sprayed onto the outer surface of the stent. The drug combination elutes from the polymeric matrix over time and enters the surrounding tissue. The drug combination preferably remains on the stent for at least three days up to approximately six months, and more preferably between seven and thirty days.

Any number of non-erodible polymers may be utilized in conjunction with the drug combination. Polymers that can be used for coatings in this application can be absorbable or non-absorbable and must be biocompatible to minimize irritation to the vessel wall. The polymer may be either biostable or bioabsorbable depending on the desired rate of release or the desired degree of polymer stability, but a bioabsorbable polymer is preferred since, unlike biostable polymer, it will not be present long after implantation to cause any adverse, chronic local response. Furthermore, bioabsorbable polymers do not present the risk that over extended periods of time there could be an adhesion loss between the stent and coating caused by the stresses of the biological environment that could dislodge the coating and introduce further problems even after the stent is encapsulated in tissue.

Suitable bioabsorbable polymers that could be used include polymers selected from the group consisting of aliphatic polyesters, poly(amino acids), copoly(ether-esters), polyalkylenes oxalates, polyamides, poly(iminocarbonates), polyorthoesters, polyoxaesters, polyamidoesters, polyoxaesters containing amido groups, poly(anhydrides), polyphosphazenes, biomolecules and blends thereof. For the purpose of this invention aliphatic polyesters include homopolymers and copolymers of lactide (which includes lactic acid d-, 1- and meso lactide), epsilon.-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, 6,6-dimethyl-1,4-2-one and polymer blends thereof. Poly(iminocarbonate) for the purpose of this invention include as described by Kemnitzer and Kohn, in the Handbook of Biodegradable Polymers, edited by Domb, Kost and Wisemen, Hardwood Academic Press, 1997, pages 251-272. Copoly(ether-esters) for the purpose of this invention include those copolyester-ethers described in Journal of Biomaterials Research, Vol. 22, pages 993-1009, 1988 by Cohn and Younes and Cohn, Polymer Preprints (ACS Division of Polymer Chemistry) Vol. 30(1), page 498, 1989 (e.g. PEO/PLA). Polyalkylene oxalates for the purpose of this invention include U.S. Pat. Nos. 4,208,511; 4,141,087; 4,130,639; 4,140,678; 4,105,034; and 4,205,399 (incorporated by reference herein). Polyphosphazenes, co-, ter- and higher order mixed monomer based polymers made from L-lactide, D,L-lactide, lactic acid, glycolide, glycolic acid, para-dioxanone, trimethylene carbonate and .epsilon.-caprolactone such as are described by Allcock in The Encyclopedia of Polymer Science, Vol. 13, pages 31-41, Wiley Intersciences, John Wiley & Sons, 1988 and by Vandorpe, Schacht, Dejardin and Lemmouchi in the Handbook of Biodegradable Polymers, edited by Domb, Kost and Wisemen, Hardwood Academic Press, 1997, pages 161-182 (which are hereby incorporated by reference herein). Polyanhydrides from diacids of the form HOOC—$C_6H_4$—O—$(CH_2)_m$—O—$C_6H_4$—COOH where m is an integer in the range of from 2 to 8 and copolymers thereof with aliphatic alpha-omega diacids of up to 12 carbons. Polyoxaesters polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213 and 5,700,583; (which are incorporated herein by reference). Polyorthoesters such as those described by Heller in Handbook of Biodegradable Polymers, edited by Domb, Kost and Wisemen, Hardwood Academic Press, 1997, pages 99-118 (hereby incorporated herein by reference). Polymeric biomolecules for the purpose of this invention include naturally occurring materials that may be enzymatically degraded in the human body or are hydrolytically unstable in the human body such as fibrin, fibrinogen, collagen, elastin, and absorbable biocompatable polysaccharides such as chitosan, starch, fatty acids (and esters thereof), glucoso-glycans and hyaluronic acid.

Suitable biostable polymers with relatively low chronic tissue response, such as polyurethanes, silicones, poly(meth)acrylates, polyesters, polyalkyl oxides (polyethylene oxide), polyvinyl alcohols, polyethylene glycols and polyvinyl pyrrolidone, as well as, hydrogels such as those formed from crosslinked polyvinyl pyrrolidinone and polyesters could also be used. Other polymers could also be used if they can be dissolved, cured or polymerized on the stent. These include polyolefins, polyisobutylene and ethylene-alphaolefin copolymers; acrylic polymers (including methacrylate) and copolymers, vinyl halide polymers and copolymers, such as polyvinyl chloride; polyvinyl ethers, such as polyvinyl methyl ether; polyvinylidene halides such as polyvinylidene fluoride and polyvinylidene chloride; polyacrylonitrile, polyvinyl ketones; polyvinyl aromatics such as polystyrene; polyvinyl esters such as polyvinyl acetate; copolymers of vinyl monomers with each other and olefins, such as ethylene-methyl methacrylate copolymers, acrylonitrile-styrene copolymers, ABS resins and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate, cellulose, cellulose acetate, cellulose acetate butyrate; cellophane; cellulose nitreate; cellulose propionate; cellulose ethers (i.e., carboxymethyl cellulose and hydroxyalkyl celluloses); and combinations thereof. Polyamides for the purpose of this application would also include polyamides of the form $-NH-(CH_2)_n-CO-$ and $NH-(CH_2)_x-NH-CO-(CH_2)_y-CO$, wherein n is preferably an integer in from 6 to 13; x is an integer in the range of form 6 to 12; and y is an integer in the range of from 4 to 16. The list provided above is illustrative but not limiting.

In certain embodiments, the polymers used for coatings have molecular weights high enough as to not be waxy or tacky. The polymers preferably adhere to the stent and are readily deformable after deposition on the stent as to be able to be displaced by hemodynamic stresses. The polymers molecular weight be high enough to provide sufficient toughness so that the polymers will not to be rubbed off during handling or deployment of the stent and not crack during expansion of the stent, though cracking can be avoided by careful placement of the coating, e.g., on portions of the stent which do not change shape between expanded and collapsed forms. The melting point of the polymer used in the present invention should have a melting temperature above 40° C., preferably above about 45° C., more preferably above 50° C. and most preferably above 55° C.

Coating may be formulated by mixing one or more of the therapeutic agents with the coating polymers in a coating mixture. The therapeutic agent may be present as a liquid, a finely divided solid, or any other appropriate physical form. Optionally, the mixture may include one or more additives, e.g., nontoxic auxiliary substances such as diluents, carriers, excipients, stabilizers or the like. Other suitable additives may be formulated with the polymer and pharmaceutically active agent or compound. For example, hydrophilic polymers selected from the previously described lists of biocompatible film forming polymers may be added to a biocompatible hydrophobic coating to modify the release profile (or a hydrophobic polymer may be added to a hydrophilic coating to modify the release profile). One example would be adding a hydrophilic polymer selected from the group consisting of polyethylene oxide, polyvinyl pyrrolidone, polyethylene glycol, carboxylmethyl cellulose, hydroxymethyl cellulose and combination thereof to an aliphatic polyester coating to modify the release profile. Appropriate relative amounts can be determined by monitoring the in vitro and/or in vivo release profiles for the therapeutic agents.

In one exemplary embodiment, which can be useful where the drugs are provided as individual monomers rather than as co-drugs, the polymeric matrix comprises two layers. The base layer comprises a solution of poly(ethylene-covinylacetate) and polybutylmethacrylate. The drug combination is incorporated into this base layer. The outer layer comprises only polybutylmethacrylate and acts as a diffusion barrier to prevent the drug combination from eluting too quickly. The thickness of the outer layer or top coat determines the rate at which the drug combination elutes from the matrix. Essentially, the drug combination elutes from the matrix by diffusion through the polymer matrix. Polymers are permeable, thereby allowing solids, liquids and gases to escape therefrom. The total thickness of the polymeric matrix is in the range from about one micron to about twenty microns or greater. It is important to note that primer layers and metal surface treatments may be utilized before the polymeric matrix is affixed to the medical device. For example, acid cleaning, alkaline (base) cleaning, salinization and parylene deposition may be used as part of the overall process described below.

To further illustrate, a poly(ethylene-co-vinylacetate), polybutylmethacrylate and drug combination solution may be incorporated into or onto the stent in a number of ways. For example, the solution may be sprayed onto the stent or the stent may be dipped into the solution. Other methods include spin coating and RF plasma polymerization. In one exemplary embodiment, the solution is sprayed onto the stent and then allowed to dry. In another exemplary embodiment, the solution may be electrically charged to one polarity and the stent electrically changed to the opposite polarity. In this manner, the solution and stent will be attracted to one another. In using this type of spraying process, waste may be reduced and more precise control over the thickness of the coat may be achieved.

In another exemplary embodiment, the drug combination or other therapeutic agent may be incorporated into a polyfluoro copolymer comprising an amount of a first moiety selected from the group consisting of polymerized vinylidenefluoride and polymerized tetrafluoroethylene, and an amount of a second moiety other than the first moiety and which is copolymerized with the first moiety, thereby producing the polyfluoro copolymer, the second moiety being capable of providing toughness or elastomeric properties to the polyfluoro copolymer, wherein the relative amounts of the first moiety and the second moiety are effective to provide the coating and film produced therefrom with properties effective for use in treating implantable medical devices.

In one embodiment according to the present invention, the exterior surface of the expandable tubular stent of the intraluminal medical device of the present invention comprises a coating according to the present invention. The exterior surface of a stent having a coating is the tissue-contacting surface and is biocompatible. The "sustained release drug delivery system coated surface" is synonymous with "coated surface", which surface is coated, covered or impregnated with sustained release drug delivery system according to the present invention.

In an alternate embodiment, the interior luminal surface or entire surface (i.e., both interior and exterior surfaces) of the elongate radially expandable tubular stent of the intraluminal medical device of the present invention has the coated surface. The interior luminal surface having the inventive sustained release drug delivery system coating is also the fluid contacting surface, and is biocompatible and blood compatible.

In certain embodiments, the device, e.g., a stent, may have two or more coatings, each of which may include a different pharmaceutically active agent. The coatings may be of the same or different polymeric material. For example, a device may have a first coating that has low permeability, and a second coating, disposed on the first coating (which may or may not completely cover the first coating) that has high permeability. The first coating may include a drug, such as 5-FU, that has high solubility in biological media, and the second coating may include a drug, such as TA, that has low solubility in biological media. Arranged in this way, the low-solubility agent, being in closer contact with the external environment, may be delivered into the environment at a rate similar to that of the high-solubility agent, the release of which is impeded by the second coating, whereas if the two agents were present in the same coating, the agent with the higher solubility would be released more rapidly than the less soluble agent.

In certain embodiments, the device, such as a stent, may be coated with a non-polymeric coating, preferably a porous coating, that includes (e.g., is impregnated with, or is admixed with) one or more pharmaceutically active compounds. Such coatings may include ceramic materials, organic materials substantially insoluble in physiologic fluids, and other suitable coatings, as will be understood by those of skill in the art. In certain other embodiments, the surface of the device itself is porous, e.g., the device may be formed of a porous material such as a ceramic or specially fabricated polymeric material, or the device may be formed in such a way that the surface achieves a porous character, and the pharmaceutically active compound is carried in the pores of the device's surface, thereby permitting gradual release of the compound upon introduction into a biological environment. In certain embodiments, the compound is 5-FU and/or TA. The surface of the device may further be coated with a polymeric material, e.g., that modulates the release of the agent(s), that improves biocompatibility, or otherwise improves the performance of the device in the medical treatment.

Another aspect of the invention relates to a device having a matrix, such as a fibrous matrix, such as a woven or non-woven cloth, e.g., vascular gauze (such as a Gortex® gauze), in which one or more pharmaceutically active compounds are disposed. In certain embodiments, the matrix is disposed on a stent, either wrapped around individual elements (e.g., wires) of the frame, or enveloping the entire device.

U.S. Pat. Nos. 5,773,019, 6,001,386, and 6,051,576 disclose implantable controlled-release devices and drugs and are incorporated in their entireties herein by reference. The inventive process for making a surface coated stent includes deposition onto the stent of a coating by, for example, dip coating or spray coating. In the case of coating one side of the stent, only the surface to be coated is exposed to the dip or spray. The treated surface may be all or part of an interior luminal surface, an exterior surface, or both interior and exterior surfaces of the intraluminal medical device. The stent may be made of a porous material to enhance deposition or coating into a plurality of micropores on or in the applicable stent surface, wherein the microporous size is preferably about 100 microns or less.

Problems associated with treating restinosis and neointimal hyperplasia can be addressed by the choice of pharmaceutical agent used to coat the stent. In certain preferred embodiments of the present invention, the chosen pharmaceutical agent is a moiety of low solubility and comprises at least two pharmaceutically active compounds. The pharmaceutically active compounds can be the same or different chemical species, and can be formed, as desired, in equimolar or non-equimolar concentrations to provide optimal treatment based on the relative activities and other pharmaco-kinetic properties of the compounds. The drug combination, particularly where co-drug formulations are used, may itself be advantageously relatively insoluble in physiologic fluids, such as blood and blood plasma, and has the property of regenerating any or all of the pharmaceutically active compounds when dissolved in physiologic fluids. In other words, to the extent that the low-solubility agent dissolves in physiologic fluids, it is quickly and efficiently converted into the constituent pharmaceutically active compounds upon dissolution. The low-solubility of the pharmaceutical agent thus insures persistence of the agent in the vicinity of an intraluminal lesion. The quick conversion of the low-solubility pharmaceutical agent into the constituent pharmaceutically active compounds insures a steady, controlled, dose of the pharmaceutically active compounds near the site of the lesion to be treated.

Examples of a suitable first pharmaceutically active compound include immune response modifiers such as cyclosporin A and FK506, corticosteroids such as dexamethasone, fluocinolone acetonide and triamcinolone acetonide, angiostatic steroids such as trihydroxy steroids, antibiotics including ciprofloxacin, differentiation modulators such as retinoids (e.g., trans-retinoic acid, cis-retinoic acid and analogues), anticancer/anti-proliferative agents such as 5-fluorouracil (5FU) and carmustine (BCNU), and non-steroidal anti-inflammatory agents such as naproxen, diclofenac, indomethacin and flurbiprofen.

In some embodiments according to the present invention, the preferred first pharmaceutically active compound is 5FU.

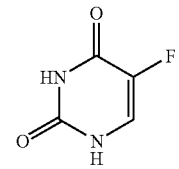

5-Fluorouracil (5FU).

Examples of a suitable second pharmaceutically active compound include immune response modifiers such as cyclosporin A and FK 506, corticosteroids such as dexamethasone, fluocinolone acetonide and triamcinolone acetonide, angiostatic steroids such as trihydroxy steroids, antibiotics including ciprofloxacin, differentiation modulators such as retinoids (e.g., trans-retinoic acid, cis-retinoic acid and analogues), anticancer/anti-proliferative agents such as 5FU and BCNU, and non-steroidal anti-inflammatory agents such as naproxen, diclofenac, indomethacin and flurbiprofen.

In some embodiments according to the present invention, the second pharmaceutically active compound is selected from fluocinolone acetonide, triamcinolone acetonide, diclofenac, and naproxen.

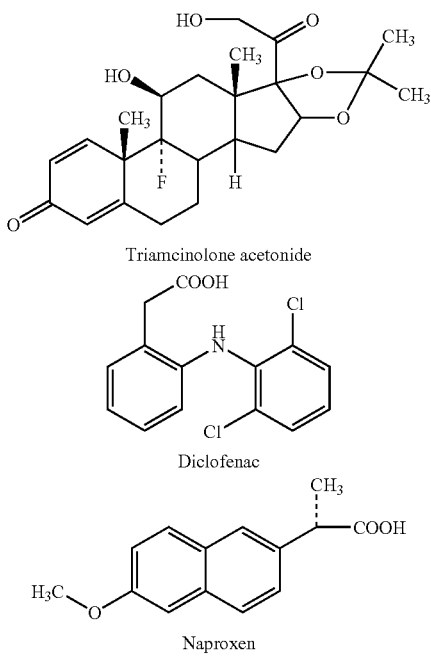

Triamcinolone acetonide

Diclofenac

Naproxen

The low-solubility pharmaceutically active agent according to the present invention may comprise further residues of pharmaceutically active compounds. Such further pharmaceutically active compounds include immune response modifiers such as cyclosporin A and FK 506, corticosteroids such as dexamethasone, fluocinolone acetonide and triamcinolone acetonide, angiostatic steroids such as trihydroxy steroids, antibiotics including ciprofloxacin, differentiation modulators such as retinoids (e.g., trans-retinoic acid, cis-retinoic acid and analogues), anticancer/anti-proliferative agents such as 5FU and BCNU, and non-steroidal anti-inflammatory agents such as naproxen, diclofenac, indomethacin and flurbiprofen.

In certain embodiments, the low-solubility pharmaceutical agent comprises a moiety of at least two pharmaceutically active compounds that can be covalently bonded, connected through a linker, ionically combined, or combined as a mixture.

In some embodiments according to the present invention, the first and second pharmaceutically active compounds are covalently bonded directly to one another. Where the first and second pharmaceutically active compounds are directly bonded to one another by a covalent bond, the bond may be formed by forming a suitable covalent linkage through an active group on each active compound. For instance, an acid group on the first pharmaceutically active compound may be condensed with an amine, an acid or an alcohol on the second pharmaceutically active compound to form the corresponding amide, anhydride or ester, respectively.

In addition to carboxylic acid groups, amine groups, and hydroxyl groups, other suitable active groups for forming linkages between pharmaceutically active moieties include sulfonyl groups, sulfhydryl groups, and the haloic acid and acid anhydride derivatives of carboxylic acids.

In other embodiments, the pharmaceutically active compounds may be covalently linked to one another through an intermediate linker. The linker advantageously possesses two active groups, one of which is complementary to an active group on the first pharmaceutically active compound, and the other of which is complementary to an active group on the second pharmaceutically active compound. For example, where the first and second pharmaceutically active compounds both possess free hydroxyl groups, the linker may suitably be a diacid, which will react with both compounds to form a diether linkage between the two residues. In addition to carboxylic acid groups, amine groups, and hydroxyl groups, other suitable active groups for forming linkages between pharmaceutically active moieties include sulfonyl groups, sulfhydryl groups, and the haloic acid and acid anhydride derivatives of carboxylic acids.

Suitable linkers are set forth in Table 1 below.

TABLE 1

| First Pharmaceutically Active Compound Active Group | Second Pharmaceutically Active Compound Active Group | Suitable Linker |
|---|---|---|
| Amine | Amine | Diacid |
| Amine | Hydroxy | Diacid |
| Hydroxy | Amine | Diacid |
| Hydroxy | Hydroxy | Diacid |
| Acid | Acid | Diamine |
| Acid | Hydroxy | Amino acid, hydroxyalkyl acid, sulfhydrylalkyl acid |
| Acid | Amine | Amino acid, hydroxyalkyl acid, sulfhydrylalkyl acid |

Suitable diacid linkers include oxalic, malonic, succinic, glutaric, adipic, pimelic, suberic, azelaic, sebacic, maleic, fumaric, tartaric, phthalic, isophthalic, and terephthalic acids. While diacids are named, the skilled artisan will recognize that in certain circumstances the corresponding acid halides or acid anhydrides (either unilateral or bilateral) are preferred as linker reagents. A preferred anhydride is succinic anhydride. Another preferred anhydride is maleic anhydride. Other anhydrides and/or acid halides may be employed by the skilled artisan to good effect.

Suitable amino acids include γ-butyric acid, 2-aminoacetic acid, 3-aminopropanoic acid, 4-aminobutanoic acid, 5-aminopentanoic acid, 6-aminohexanoic acid, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. Again, the acid group of the suitable amino acids may be converted to the anhydride or acid halide form prior to their use as linker groups.

Suitable diamines include 1, 2-diaminoethane, 1,3-diaminopropane, 1,4-diaminobutane, 1,5-diaminopentane, 1,6-diaminohexane.

Suitable aminoalcohols include 2-hydroxy-1-aminoethane, 3-hydroxy-1-aminoethane, 4-hydroxy-1-aminobutane, 5-hydroxy-1-aminopentane, 6-hydroxy-1-aminohexane.

Suitable hydroxyalkyl acids include 2-hydroxyacetic acid, 3-hydroxypropanoic acid, 4-hydroxybutanoic acid, 5-hydroxypentanoic acid, 5-hydroxyhexanoic acid.

The person having skill in the art will recognize that by selecting first and second pharmaceutical moieties (and optionally third, etc. pharmaceutical moieties) having suitable active groups, and by matching them to suitable linkers, a broad palette of inventive compounds may be prepared within the scope of the present invention.

Exemplary preferred low-solubility pharmaceutically active agents according to the present invention include 5FU covalently bonded to fluocinolone acetonide, 5FU covalently bonded to diclofenac, and 5FU covalently bonded to naproxen. Illustrative examples include the following:

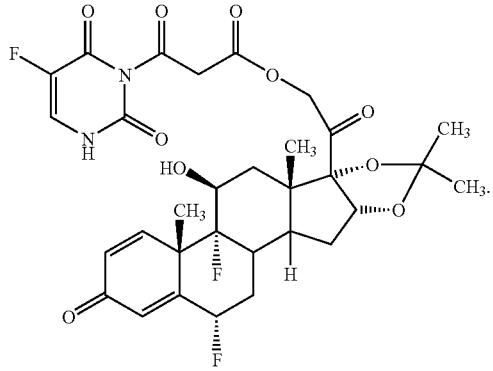

5FU-fluocinolone acetonide (via oxalate linker)

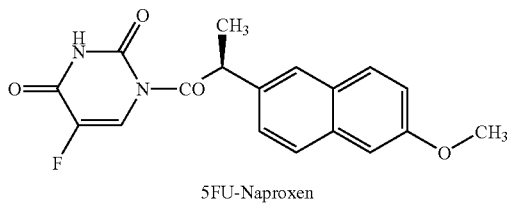

5FU-Naproxen

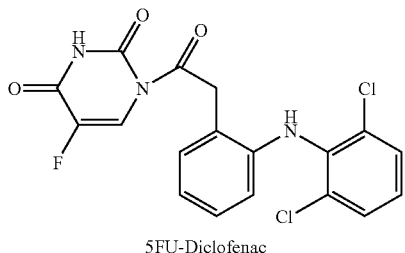

5FU-Diclofenac

In other embodiments, the first and second pharmaceutically active compounds may be combined to form a salt. For instance, the first pharmaceutically active compound may be an acid, and the second pharmaceutically active compound may be a base, such as an amine. As a specific example, the first pharmaceutically active compound may be diclofenac or naproxen (acids), and the second pharmaceutically active compound may be ciprofloxacin (a base). The combination of diclofenac and ciprofloxacin would for instance form the salt:

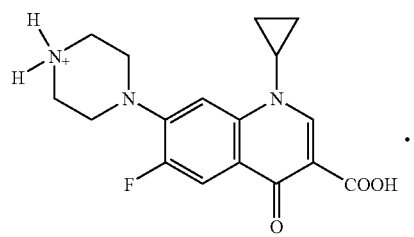

-continued

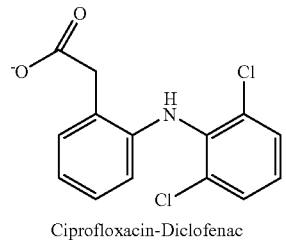

Ciprofloxacin-Diclofenac

In still other embodiments, the first and second pharmaceutically active compounds may be combined as a mixture.

As used in regard to the low-solubility pharmaceutical agent, the term "low-solubility" relates to the solubility of the pharmaceutical agent in biological fluids, such as blood plasma, lymphatic fluid, peritoneal fluid, etc. In general, "low-solubility" means that the pharmaceutical agent is only very slightly soluble in aqueous solutions having pH in the range of about 5 to about 8, and in particular to physiologic solutions, such as blood, blood plasma, etc. Some low-solubility agents according to the present invention will have solubilities of less than about 100 µg/ml, preferably less than about 20 µg/ml, more preferably less than about 15 µg/ml, and more preferably, less than about 10 µg/ml. Solubility is in water at a temperature of 25° C. as measured by the procedures set forth in the 1995 USP, unless otherwise stated. This includes compounds which are slightly soluble (about 10 mg/ml to about 1 mg/ml), very slightly soluble (about 1 mg/ml to about 0.1 mg/ml) and practically insoluble or insoluble compounds (less than about 0.1 mg/ml).

Inventive compounds are slowly dissolved in physiologic fluids, but are relatively quickly dissociated into at least first and second pharmaceutically active compounds upon dissolution in physiologic fluids. In some embodiments the dissolution rate of the inventive compounds is in the range of about 0.001 µg/day to about 10 µg/day. In certain embodiments, the inventive compounds have dissolution rates in the range of about 0.01 to about 1 µg/day. In particular embodiments, the inventive compounds have dissolution rates of about 0.1 µg/day.

The low-solubility pharmaceutical agent is incorporated into a biocompatible (i.e. biologically tolerated) polymer coating. In some embodiments according to the present invention, the low-solubility pharmaceutical agent is present as a plurality of granules dispersed within the polymer coating. In such cases, it is preferred that the low-solubility pharmaceutical agent be relatively insoluble in the polymer coating, however the low-solubility pharmaceutical agent may possess a finite solubility coefficient with respect to the polymer coating and still be within the scope of the present invention. In either case, the polymer coating solubility of the low-solubility pharmaceutical agent should be such that the agent will disperse throughout the polymer coating, while remaining in substantially granular form.

In some embodiments according to the present invention, the low-solubility pharmaceutical agent is dissolved within the polymer coating. In such cases, it is preferred that the polymer coating be a relatively non-polar or hydrophobic polymer which acts as a good solvent for the relatively hydrophobic low-solubility pharmaceutical agent. In such cases, the solubility of the low-solubility pharmaceutical agent in the polymer coating should be such that the agent will dissolve thoroughly in the polymer coating, being distributed homogeneously throughout the polymer coating.

In some embodiments according to the present invention, the polymer is non-bioerodible. Examples of non-bioerodible polymers useful in the present invention include poly (ethylene-co-vinyl acetate) (EVA), polyvinylalcohol and polyurethanes, such as polycarbonate-based polyurethanes. In other embodiments of the present invention, the polymer is bioerodible. Examples of bioerodible polymers useful in the present invention include polyanhydride, polylactic acid, polyglycolic acid, polyorthoester, polyalkylcyanoacrylate or derivatives and copolymers thereof. The skilled artisan will recognize that the choice of bioerodibility or non-bioerodibility of the polymer depends upon the final physical form of the system, as described in greater detail below. Other exemplary polymers include polysilicone and polymers derives from hyaluronic acid. The skilled artisan will understand that the polymer according to the present invention is prepared under conditions suitable to impart permeability such that it is not the principal rate determining factor in the release of the low-solubility agent from the polymer.

Moreover, suitable polymers include naturally occurring (collagen, hyaluronic acid) or synthetic materials that are biologically compatible with bodily fluids and mammalian tissues, and essentially insoluble in bodily fluids with which the polymer will come in contact. In addition, the suitable polymers essentially prevent interaction between the low-solubility agent dispersed/suspended in the polymer and proteinaceous components in the bodily fluid. The use of rapidly dissolving polymers or polymers highly soluble in bodily fluid or which permit interaction between the low-solubility agent and proteinaceous components are to be avoided since dissolution of the polymer or interaction with proteinaceous components would affect the constancy of drug release. Other suitable polymers include polypropylene, polyester, polyethylene vinyl acetate (EVA), polyethylene oxide (PEO), polypropylene oxide, polycarboxylic acids, polyalkylacrylates, cellulose ethers, polyalkyl-alkyacrylate copolymers, polyester-polyurethane block copolymers, polyether-polyurethane block copolymers, polydioxanone, poly-($\beta$-hydroxybutyrate), polylactic acid (PLA), polycaprolactone, polyglycolic acid, and PEO-PLA copolymers.

The coating of the present invention may be formed by mixing one or more suitable monomers and a suitable low-solubility pharmaceutical agent, then polymerizing the monomer to form the polymer system. In this way, the agent is dissolved or dispersed in the polymer. In other embodiments, the agent is mixed into a liquid polymer or polymer dispersion and then the polymer is further processed to form the inventive coating. Suitable further processing includes crosslinking with suitable crosslinking agents, further polymerization of the liquid polymer or polymer dispersion, copolymerization with a suitable monomer, block copolymerization with suitable polymer blocks, etc. The further processing traps the drug in the polymer so that the drug is suspended or dispersed in the polymer coating.

In some embodiments according to the present invention, monomers for forming a polymer are combined with an inventive low-solubility compound and are mixed to make a homogeneous dispersion of the inventive compound in the monomer solution. The dispersion is then applied to a stent according to a conventional coating process, after which the crosslinking process is initiated by a conventional initiator, such as UV light. In other embodiments according to the present invention, a polymer composition is combined with an inventive low-solubility compound to form a dispersion. The dispersion is then applied to a stent and the polymer is cross-linked to form a solid coating. In other embodiments according to the present invention, a polymer and an inventive low-solubility compound are combined with a suitable solvent to form a dispersion, which is then applied to a stent in a conventional fashion. The solvent is then removed by a conventional process, such as heat evaporation, with the result that the polymer and inventive low-solubility drug (together forming a sustained-release drug delivery system) remain on the stent as a coating.

An analogous process may be used where the inventive low-solubility pharmaceutical compound is dissolved in the polymer composition.

In some embodiments according to the invention, the system comprises a polymer that is relatively rigid. In other embodiments, the system comprises a polymer that is soft and malleable. In still other embodiments, the system includes a polymer that has an adhesive character. Hardness, elasticity, adhesive, and other characteristics of the polymer may be varied as necessary.

In some embodiments according to the present invention, the polymer is non-bioerodible, or is bioerodible only at a rate slower than a dissolution rate of the low-solubility pharmaceutical agent, and the diameter of the granules is such that when the coating is applied to the stent, the granules' surfaces are exposed to the ambient tissue. In such embodiments, dissolution of the low-solubility pharmaceutical agent is proportional to the exposed surface area of the granules.

In other embodiments according to the present invention, the polymer coating is permeable to water in the surrounding tissue, e.g. in blood plasma. In such cases, water solution may permeate the polymer, thereby contacting the low-solubility pharmaceutical agent. The rate of dissolution may be governed by a complex set of variables, such as the polymer's permeability, the solubility of the low-solubility pharmaceutical agent, the pH, ionic strength, and protein composition, etc. of the physiologic fluid. In certain embodiments, however the permeability may be adjusted so that the rate of dissolution is governed primarily, or in some cases practically entirely, by the solubility of the low-solubility pharmaceutical agent in the ambient liquid phase. In still other embodiments the pharmaceutical agent may have a high solubility in the surrounding fluid. In such cases the matrix permeability may be adjusted so that the rate of dissolution is governed primarily, or in some cases practically entirely, by the permeability of the polymer.

EXAMPLES

The present invention can be more fully understood with reference to the following examples.

Agent TC-112 comprising a conjugate of 5-fluorouracil and naproxen linked via a reversible covalent bond, and agent G.531.1, comprising a conjugate of 5-fluorouracil and fluocinolone acetonide, were prepared in accordance with the methods set forth in U.S. Pat. No. 6,051,576. The structure of these compounds is reproduced below.

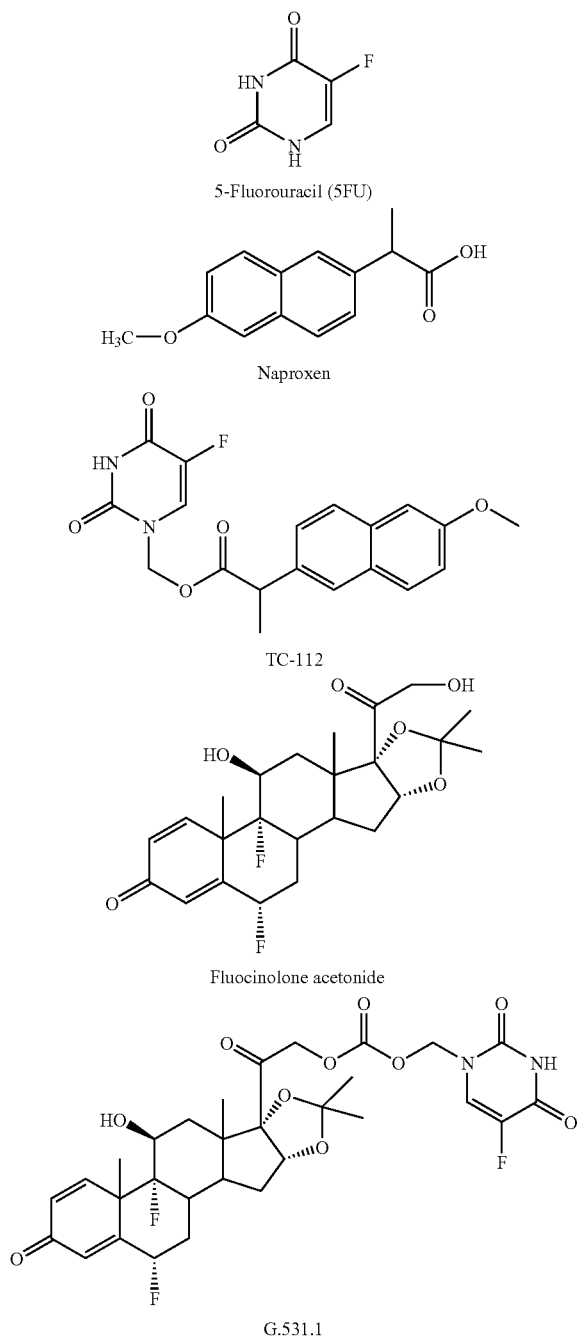

The following examples are intended to be illustrative of the disclosed invention. The examples are non-limiting, and the skilled artisan will recognize that other embodiments are within the scope of the disclosed invention.

Example 1

To 20 gm of 10% (w/v) aqueous poly(vinyl alcohol) (PVA) solution, 80.5 mg of agent TC-112 was dispersed. 5 pieces of glass plates were then dipping coated with this TC-112/PVA suspension and followed by air-drying. The coating and air-drying was repeated four more times. At the end about 100 mg of TC-112/PVA was coated on each glass plates. The coated glass plates were then heat treated at 135° C. for 5 hours. After cooling to room temperature, the glass plates were individually placed in 20 ml of 0.1 M mol phosphate buffer (pH 7.4, 37° C.) for release test. Sample was taken daily and entire release media were replaced with fresh one at each sampling time. The drugs and TC-112 released in the media were determined by reverse-phase HPLC. The half-life for TC-112 in pH 7.4 buffer is 456 min, in serum is 14 min.

Figure 3:
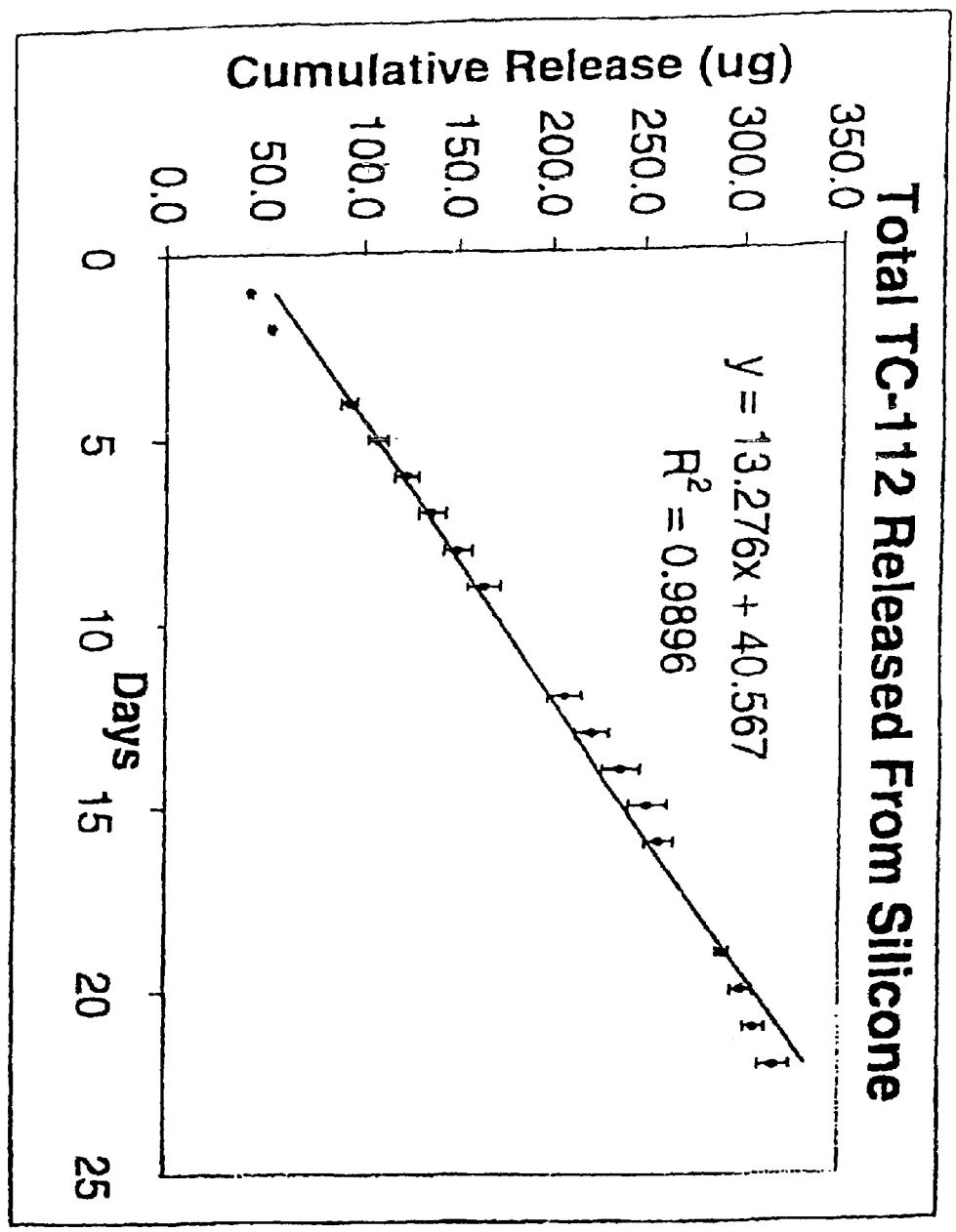
FIG. 3 is a release profile of TC-112 from PVA-coated glass slides into pH 7.4 buffer.

The results are shown in FIG. 3, which shows the total cumulative release of TC-112 from PVA coated glass plates. The slope of the curve demonstrates that TC-112 is released at 10 μg/day. The data represent both intact and constituents (5-fluorouracil and naproxen) of the compound TC-112.

Example 2

12.0 gm of silicone part A (Med-6810A) were mixed with 1.2 gm of silicone part B (Med-6810B), and degassed in sonicator for 10 min, followed by water aspirator. 41.2 mg of (TC-112) were dispersed in this degassed silicone, and degassed again. 0.2 gm of the mixture was spread on one surface of a glass plate. The glass plates (total 5) were then placed in oven and heated at 105° C. for 20 min. to cure. After removing from the oven and cooled to room temperature, 0.2 gm of the mixture was spread on the other uncoated surface of each glass plate. The coated glass plates were then heat treated again at 105° C. for 20 min. After cooling to room temperature, the glass plates were individually placed in 20 ml of 0.1 M phosphate buffer (pH 7.4, 37° C.) for release test. Samples were taken daily, and the entire release media was replaced with fresh media at each sampling time. The drugs (5-fluorouracil and naproxen) and TC-112 released in the media were determined by HPLC.

The total TC-112 release for silicone coating was calculated as follows. The molecular weight of Naproxen is 230.3, and the molecular weight for 5-Fluorouracil is 130.1, while the compound TC-112 generated from these two drugs has a molecular weight of 372.4. To detect x mg of naproxen, this means that x*372.4/230.3 mg of TC-112 was hydrolyzed. The total TC-112 released equals the sum of TC-112 detected in the release media and the TC-112 hydrolyzed. For example, up to day 6, 43.9 mg of naproxen is detected, this means 71.0 (43.9*372.4/230.3) mg of was hydrolyzed, at the same time, 51.4 mg of TC-112 is detected in buffer, therefore a total of 122.4 mg (51.4 plus 71.0) of TC-112 is released up to day 6.

Figure 4:
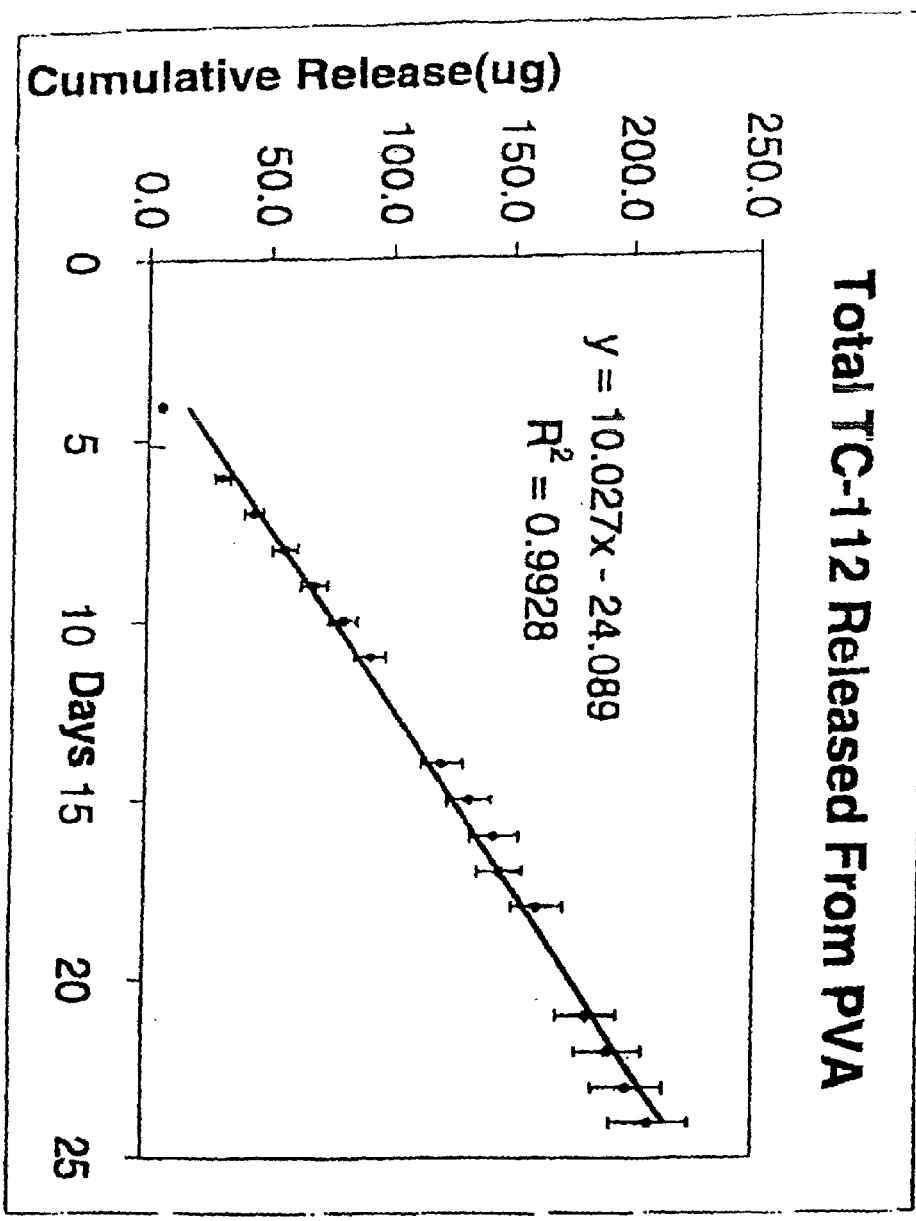
FIG. 4 is a release profile of TC-112 from silicone-coated glass plates into pH 7.4 buffer.

The results are shown in FIG. 4, which shows the total cumulative release of TC-112 from silicone coated glass plates. The slope of the curve demonstrates that TC-112 is released at 13.3 μg/day. Again, the data represent both intact and constituents of the inventive compound. The similarity in the slopes demonstrates that the polymers have little effect on the release of the drug.

Example 3

A mixture of 3.3 gm Chronoflex C(65D) (Lot# CTB-G25B-1234) dispersion containing 0.3 gm of Chronoflex C(65D) and 2.2 gm Chronoflex C(55D) (Lot# CTB-121B-1265) dispersion containing 0.2 gm of Chronoflex C (55D), both in dimethyl acetamide (DMAC) (1:10, w/w) was prepared by mixing the two dispersions together. To this mixture, 6.0 gm of tetrahydrofurane (HPLC grade) were added and mixed. The final mixture was not a clear solution. Then 101.5 mg of TC-32 was added and dissolved into the polymer solution.

Ten (10) HPLC inserts were then coated with the polymer/TC-32 solution by dipping, which was then followed by air-drying under ambient temperature. The coating and air-drying process was repeated four (4) times (5 times total) until a total of about 10 mg of polymer/CT-32 was applied to each insert. The inserts were then placed in an oven at 80° C. for two hour to remove the residue of the solvent.

Figure 5:
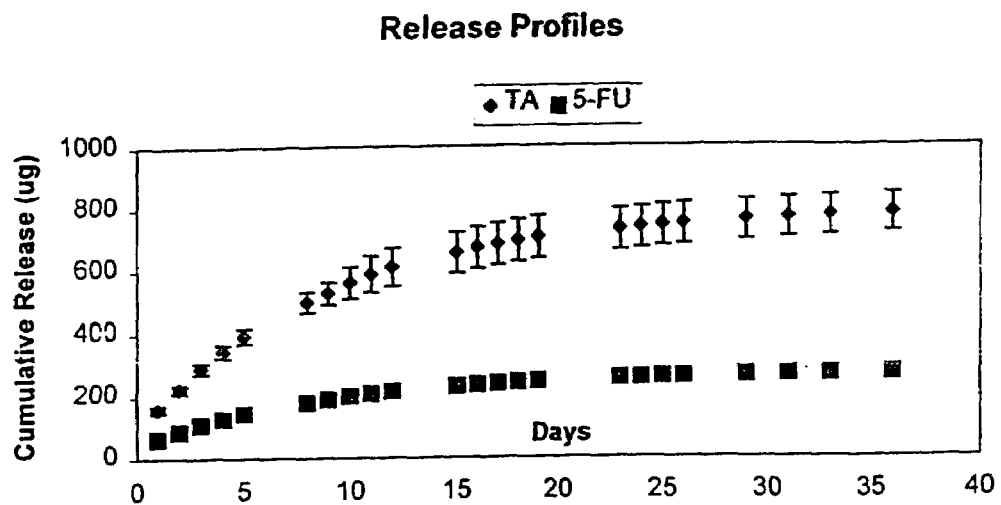
FIG. 5 is a release profile of 5-Fluroruracil (5FU) and triamcinolone acetonide (TA) from coated inserts.

The inserts were placed individually in 20 ml of 0.1 m phosphate buffer, pH 7.4, in glass tube and monitoring of the release of compounds from the inserts at 37° C. was begun. Samples were taken daily, and the entire media was replaced with fresh media at each sampling time. The drugs released in the media were determined by HPLC. TC-32 is a compound comprising 5FU linked to triamcinolone acetonide (TA). Because of the short half-life of TC-32 in buffer, no TC-32 was detectable in the release media; only amounts of parent drugs, 5FU and TA, could be determined. The release profiles are displayed in FIG. 5.

Example 4

To 5.0 gm of stirred dimethyl acetamide (DMAC), 300 mg of Chronoflex C(65D) (Lot# CTB-G25B-1234) and 200 mg of Chronoflex C(55D) (Lot# CTB-121B-1265) were added. The polymer was slowly dissolved in DMAC (about 4 hours). Then 5.0 gm of THF was added to the polymer dispersion. The mixture was not a clear solution. Then 100.9 mg of TC-32 was added and dissolved in the mixture.

Figure 6:
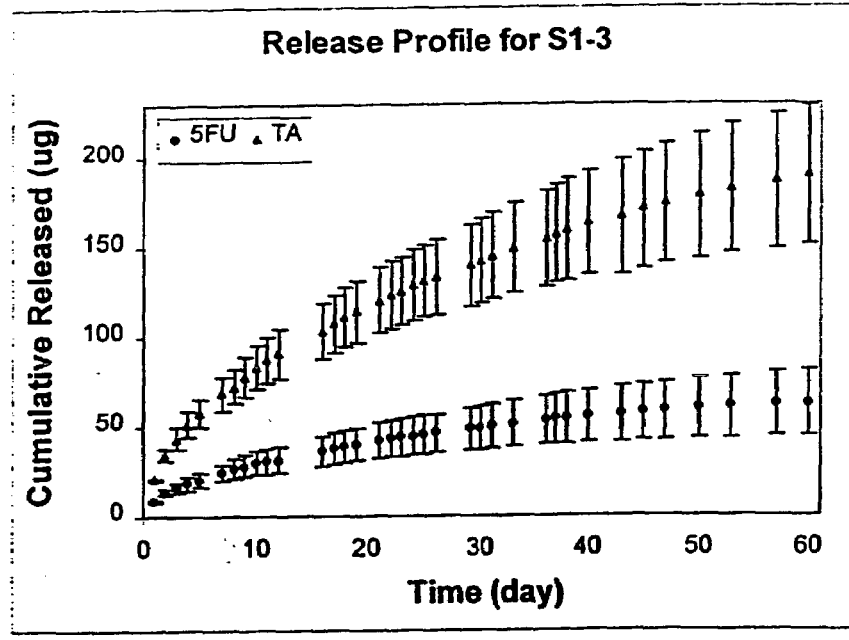
FIG. 6 is a release profile of 5-flurouracil (5FU) and triamcinolone acetonide (TA) from coated inserts.

Three (3) Stents, supplied by Guidant Corp, were coated then with the polymer /TC-32 solution by dipping and followed by air-drying under ambient temperature. The coating and air-drying process was repeated a few times till a total of about 2.0 mg of polymer/TC-32 were applied to each stent. The coated stents were air-dried under ambient temperature in a biological safety cabinet over night. The stents were then vacuum dried at 80° C. for two hour to remove the residue of the solvent. Afterwards they were placed individually in 5.0 ml of 0.1 m phosphate buffer, pH 7.4, in glass tube and monitoring of the release of compounds from the stents was at 37° C. was begun. Samples were taken daily, and the entire media was replaced with a fresh one at each sampling time. The drugs released in the media were determined by HPLC. The release profiles were shown in the FIG. 6. No TC-32 was detectable in the release media.

The purpose of the above description and examples is to illustrate some embodiments of the present invention without implying any limitation. It will be apparent to those of skill in the art that various modifications and variations may be made to the systems, devices and methods of the present invention without departing from the spirit or scope of the invention. All patents and articles cited herein are specifically incorporated herein in their entireties.

Example 5

Chronoflex C (65D, Lot# CTB-G25B-1234) was first dissolved in tetrahydrofuran. Into this solution bioreversible conjugates of 5FU and TA were dissolved and the resulting solution spray coated onto coronary Tetra stents produced by Guidant. After air-drying, the coated stents were vacuum dried at 50° C. for 2 hours to remove solvent residue, and subject to plasma treatment and gamma-irradiation. Two different levels of drug loading were applied to stents: 80 ug Low Dose (13%) and 600 ug High Dose (60%). The release rate was determined in vitro by placing the coated stents (inflated with a dialation catheter: 3.0 mm balloon size and 20 mm long) in 0.1M phosphate buffer (pH 7.4) at 37° C. Samples of the buffer solution were periodically removed for analysis by HPLC, and the buffer was replaced to avoid any saturation effects.

Figure 7:
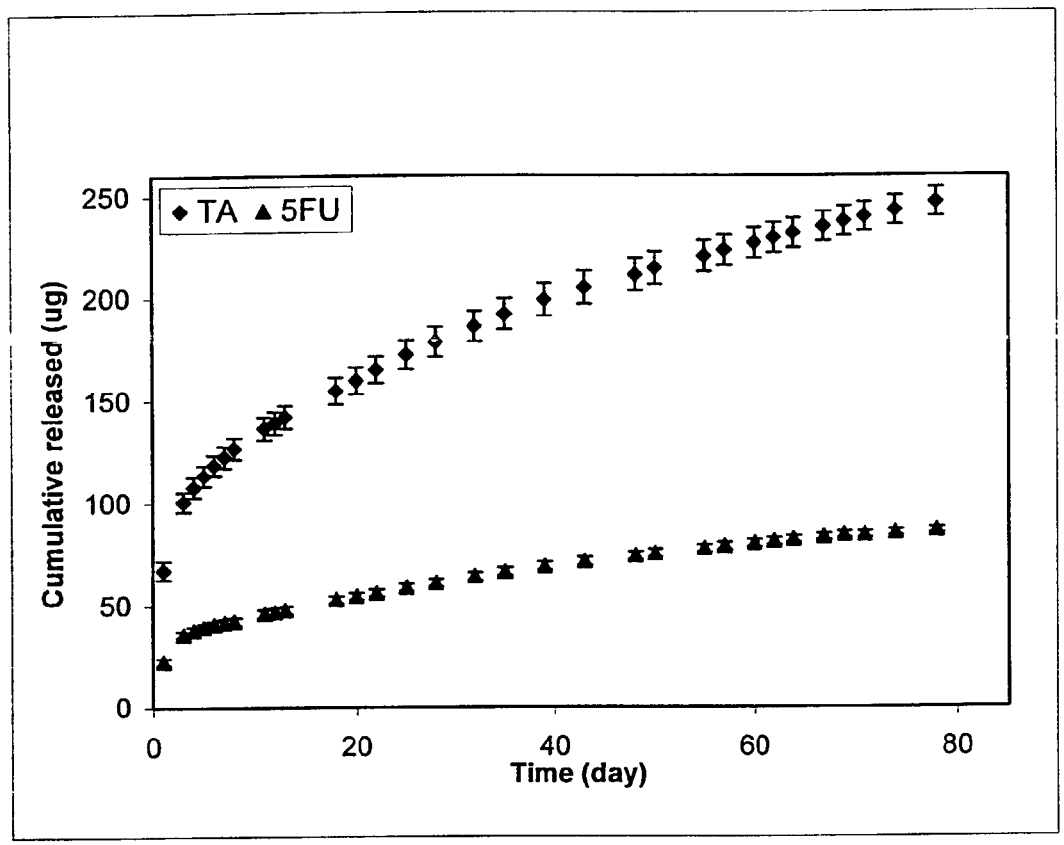
FIG. 7 illustrates the release pattern in vitro for a high dose coated stent.

The results shown in FIG. 7 illustrate the release pattern in vitro for a High Dose coated stent. The pattern followed a pseudo logarithmic pattern with approximately 70% being released in 10 weeks. A similar pattern is seen in both High Dose and Low Dose loaded stents. TA and FU were released in an equimolar fashion at all times during the experiments. No co-drugs of 5FU/TA were detectable in the release media.

Example 6

Chronoflex C (65D, Lot# CTB-G25B-1234, 1.008 gm) was added to 50.0 gm of tetrahydrofuran (THF). The mixture was stirred overnight to dissolve the polymer. 5.0 gm of the polymer solution was diluted with 10.0 gm of THF. 150.2 mg of a co-drug TC-32 (5-fluorouracil and triamcinolone acetonide) was added to the polymer solution and dissolved. The coating solution was prepared with 60% codrug loading. A 13% codrug loaded coating solution was also prepared. Bare stents (Tetra, Guidant, Lot# 1092154, 13 mm Tetra) were washed with isopropanol, air-dried, and spray coated with the coating solution using a precision airbrush. The coating was repeated until approximately 1.0 mg of total coating had been applied to each stent. After air-drying, the coated stents were vacuum dried at 50° C. for 2 hours to remove solvent residue, and subject to plasma treatment and gamma-irradiation Co-drug coated stents were tested in two groups. After inflated with a dialation catheter (3.0 mm balloon size and 20 mm long), Group One stents were placed individually into a glass tube containing 5.0 ml of 0.1 M phosphate buffer (pH 7.4). Samples were taken periodically and the concentration of co-drug in the buffer was tested by HPLC. The entire release media was replaced after each sample.

Group Two stents were placed in vivo. Three common swine had TC-32 coated stents implanted into the left anterior descending (LAD) coronary artery on study day 1. The stents were harvested on study day 5 and then placed in 0.1 M phosphate buffer as describe for Group One stents. The amount of each drug released into the media was determined by HPLC. The intact codrug was not detectable in release media.

Figure 8:
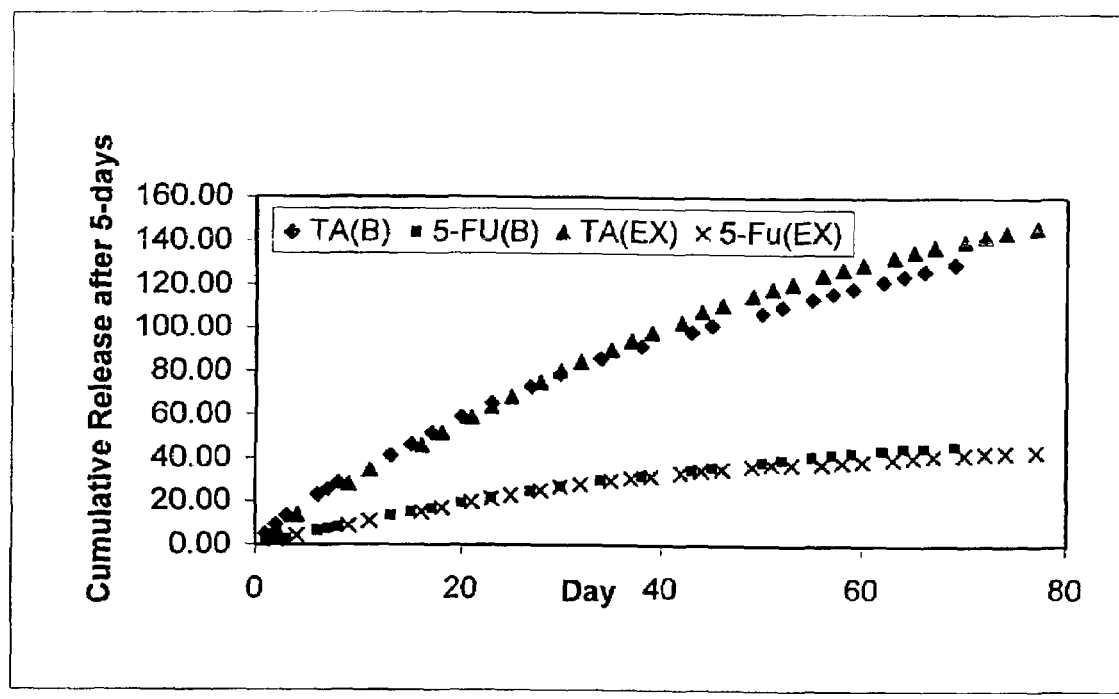
FIG. 8 shows the comparative drug release profiles between explanted stents and non-implanted stents.

The results are shown in FIG. 8, showing the comparative drug release profiles between explanted stents and non-implanted stents. The release patterns for both explanted and pre-implanted stents indicate that in-vivo release may be predicted by in vitro release patterns.

Example 7

Fourteen (14) domestic swine received a maximum of three (3) stents deployed in any of the three-epicardial coronaries (LAD, LCX, and RCA). Some animals were given only control stents, comprising either Bare Metal Tetra Coronary Stent on Cross Sail Rx balloon delivery system (Control), or PU Coated Tetra Coronary Stent on Cross Sail Rx balloon delivery system (Control). Other animals were given drug-coated stents either in Low Dose (80 μg TA+5FU (13%)) or High Dose (600 μg TA+5FU (60%)). The stents were implanted into arteries of the animals. Each stent was advanced to the desired location in the artery, and was deployed using an inflation device. The pressure of the inflation device was chosen to achieve a balloon to artery ratio of 1.1-1.2:1.

After 28 days, arterial sections directly adjacent to the stents were surgically excised and embedded in a methacrylate resin. Histologic 5-μm sections were cut and stained with Verhoeff's elastin and Hematoxylin and Eosin stains, and the thickness of each excised section was measured. The results are shown in table for both High and Low Dose drug-coated stents. The response at 28 days in both low-dose and high-dose experimental groups shows a profound reduction in intimal thickness attributed to the co-release of TA and 5FU3 from polymer coated Tetra stents

|  | Bare Metal | Polymer | Low Dose | High Dose |
|---|---|---|---|---|
| Balloon: artery ratio | 1.07 ± 0.05 | 1.11 ± 0.07 | 1.13 ± 0.05 | 1.11 ± 0.08 |
| Intimal Thickness (mm) | 0.29 ± 0.03 | 0.36 ± 0.08 | 0.13 ± 0.01$^\xi$ | 0.13 ± 0.04$^\wp$ |
| Medial area (mm$^2$) | 1.39 ± 0.10 | 1.98 ± 0.41 | 0.96 ± 0.06$^\S$ | 0.98 ± 0.07$^\zeta$ |

$^\xi$p = 0.0008 Bare Metal vs Low Dose, p = 0.03 Polymer vs Low Dose
$^\S$p = 0.002 Bare Metal vs. Low Dose, p = 0.04 Polymer vs Low Dose
$^\wp$p = 0.02 Bare Metal vs. High Dose, p = 0.07 Polymer vs. High Dose
$^\zeta$p = 0.01 Bare Metal vs High Dose, p = 0.07 Polymer vs. High Dose Example 8

Stents were coated with a mixture of TA and 5FU in a mole-ratio of 1 to 1 without chemical linkage. The release rate was determined in vitro by placing the coated stents in 0.1M phosphate buffer (pH 7.4) at 37° C. Samples of the buffer solution were periodically removed for analysis by HPLC, and the buffer was replaced to avoid any saturation effects.

Figure 9:
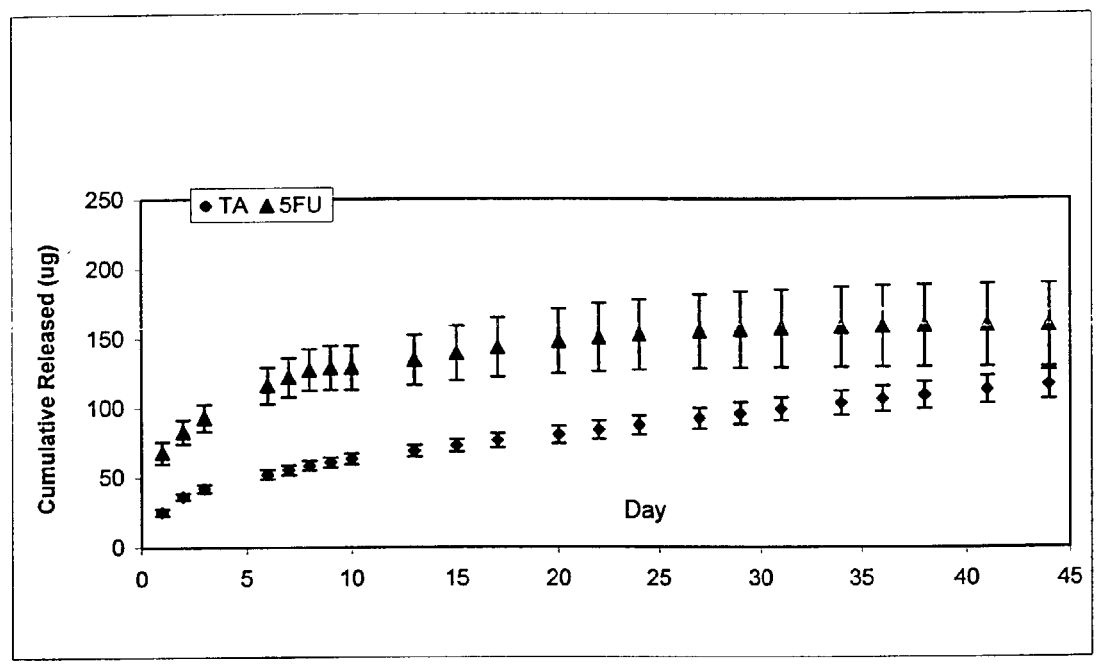
FIG. 9 shows the release rate from stents that were coated with a mixture of TA and 5FU in a mole-ratio of 1 to 1 without chemical linkage.
Figure 10A:
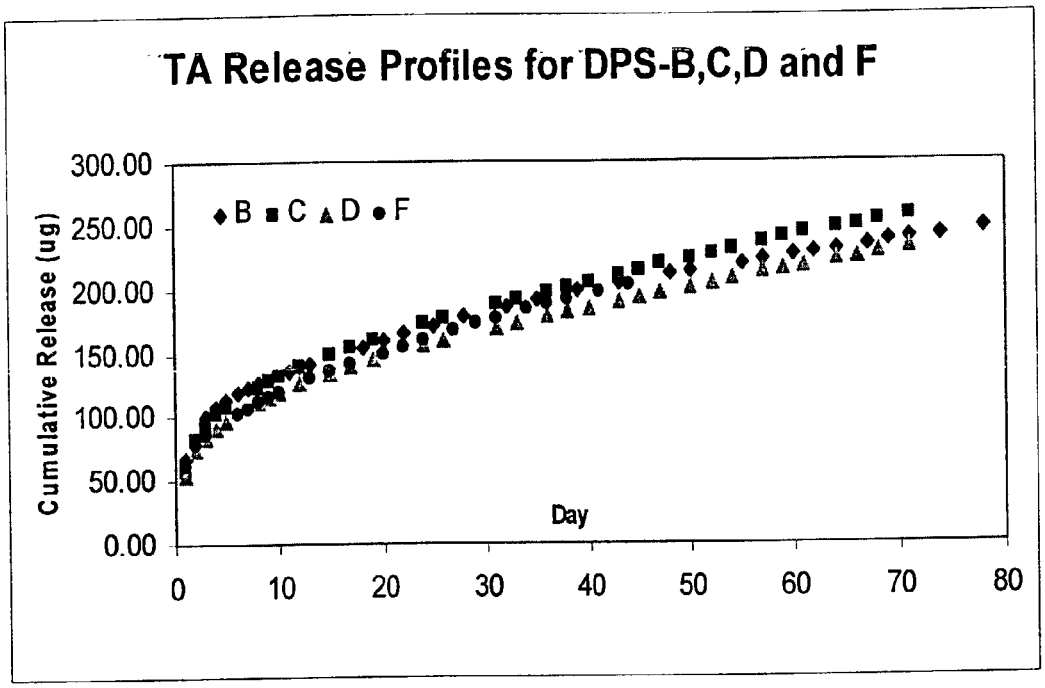
FIGS. 10A and 10B are graphs showing the effect of gamma irradiation and plasma treatment on drug release. Group B: with plasma treatment, with gamma irradiation.
Figure 10B:
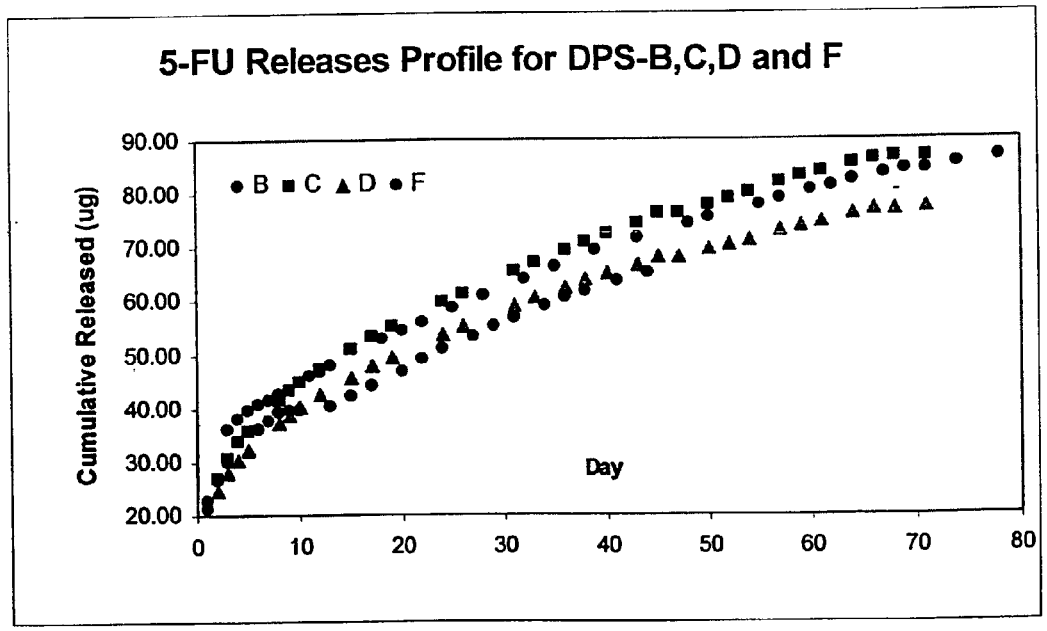

The results are shown in FIG. 9. Because of the hydrophilic nature of 5FU, this compound was released from the mixture coating much faster than from the codrug coating. Within 4 weeks, more than 95% of total 5FU was released. TA release from the drug mixture coating was much slower, with about 20% TA released over the first 6 weeks.

The 5FU/TA mixture in a polymer coating demonstrated different release profiles compared to the codrug polymer coating. However, this study indicates that use of a mixture of 5FU and TA can be applied to a stent to achieve controlled release of a desired active compound mixture.

Example 9

A polymer-coated stent was also tested to identify any inherent release pattern attributable to the polymer. Following plasma treatment and gamma-irradiation, the stents were inflated with a dilatation catheter (3.0 mm balloon size, 20 mm long) and placed individually into a glass tube containing 5.0 ml of 0.1 M phosphate buffer (pH 7.4). Samples were taken periodically and the entire release media was replaced after each sample. The amount of each drug released into the media was determined by HPLC. The intact codrug was not detectable in release media.

We claim:
1. A medical device comprising:
   (a) a substrate having a surface; and,
   (b) a coating adhered to the surface, said coating comprising a polymer matrix having a low solubility prodrug dispersed therein, wherein said low solubility prodrug is represented by the general formula A-L-B, in which

A represents a drug moiety having a therapeutically active form for producing a clinical response in a patient;
   L represents a covalent linker linking A and B to form a prodrug, said linker being cleaved under physiological conditions to generate said therapeutically active form of A; and
   B represents a moiety which, when linked to A, results in the prodrug having a lower solubility than the therapeutically active form of A and is biologically or pharmacologically inert upon cleavage from the prodrug.

2. The device of claim 1, wherein the solubility of the therapeutically active form of A in water is greater than 1 mg/mL and the solubility of the prodrug in water at 25° C. is less than 1 mg/mL.

3. The device of claim 1, which provides sustained release of the therapeutically active form of A for a period of at least 24 hours, and, over the period of release, the concentration of the prodrug eluting from polymer is less than 10% of the concentration of the therapeutically active form of A.

4. The device of claim 1, wherein the therapeutically active form of A has a logP value at least 1 logP unit less than the logP value of the prodrug.

5. The device of claim 1, wherein the solubility of the prodrug is less than 100 μg/ml in water at 25° C.

6. The device of claim 1, wherein B is a hydrophobic aliphatic moiety.

7. The device of claim 1, wherein A is selected from immune response modifiers, anti-proliferatives, anti-mitotic agents, anti-platelet agents, platinum coordination complexes, hormones, anticoagulants, fibrinolytic agents, anti-secretory agents, anti-migratory agents, immunosuppressives, angiogenic agents, angiotensin receptor blockers, nitric oxide donors, antisense oligionucleotides and combinations thereof, cell cycle inhibitors, corticosteroids, angiostatic steroids, anti-parasitic drugs, anti-glaucoma drugs, antibiotics, differentiation modulators, antiviral drugs, anti-cancer drugs and anti-inflammatory drugs.

8. The device of claim 1, wherein A is an antineoplastic agent.

9. The device of claim 8, wherein said antineoplastic agent is selected from anthracyclines, vinca alkaloids, purine analogs, pyrimidine analogs, inhibitors of pyrimidine biosynthesis, and alkylating agents.

10. The device of claim 8, wherein said antineoplastic agent is selected from 5-fluorouracil (5FU), 5'-deoxy-5-fluorouridine 5-fluorouridine, 2'-deoxy-5-fluorouridine, fluorocytosine, 5-trifluoromethyl-2'-deoxyuridine, arabinoxyl cytosine, cyclocytidine, 5-aza-2'-deoxycytidine, arabinosyl 5-azacytosine, 6-azacytidine, N-pbosphonoacetyl-L-aspartic acid, pyrazofurin, 6-azauridine, azaribine, and 3-deazauridine.

11. The device of claim 8, wherein said antineoplastic agent is selected from the group consisting of cladribine, 6-mercaptopurine, pentostatin, 6-thioguanine, and fludarabin phosphate.

12. The device of claim 8, wherein said antineoplastic agent is a pyrimidine analog.

13. The device of claim 11, wherein said pyrimidine analog is selected from the group consisting of arabinosyl cytosine, cyclocytidine, 5-aza-2'-deoxycytidine, arabinosyl 5-azacytosine and 6-azacytidine.

14. The device of claim 12, wherein the pyrimidine analog is selected from 5-fluorouracil (5FU), 5'-deoxyfluorouridine, fluorouridine, 2'-deoxyfluorouridine, fluorocytosine, trifluoro-methyl-2'-deoxyuridine, arabinosyl cytosine, cyclocytidine, 5-aza-2'-deoxycytidine, arabinosyl-5-azacytosine, 6-azacytidine, N-phosphonoacetyl-L-asparticacid (PALA), pyrazofurin, 6-azauridine, azaribine, thymidine and 3-deazauridine.

15. The device of claim 11, wherein the pyrimidine analog is a 5-fluoropyrimidine or 5-fluoropyrimidine nucleoside analog.

16. The device of claim 15, wherein the nucleoside analog is 5-fluorouracil (5FU) or a prodrug thereof.

17. The device of claim 1, wherein A is a steroid.

18. The device of claim 17, wherein the steroid is a corticosteroid.

19. The device of claim 17, wherein the steroid has a solubility less than 0.1 mg/mL in water at 25° C., dispersed or dissolved therein.

20. The device of claim 17, wherein the steroid has a logP value at least 0.5 logP units more than the logP value for dexamethasone.

21. The device of claim 17, wherein the steroid is triamcinolone or a prodrug thereof.

22. The device of claim 1, wherein A is a fluorinated pyrimidine.

23. The device of claim 1, wherein A is 5-fluorouracil.

24. The device of claim 1, wherein the linkage L is hydrolyzed in bodily fluid.

25. The device of claim 24, wherein the linkage L includes one or more hydrolyzable groups selected from an ester, an amide, a carbamate, a carbonate, a cyclic ketal, a thioester, a thioamide, a thiocarbamate, a thiocarbonate, a xanthate and a phosphate ester.

26. The device of claim 1, wherein the linkage L is enzymatically cleaved.

27. The device of claim 1, wherein the polymer is non-bioerodible.

28. The device of claim 27, wherein the non-bioerodible polymer is selected from polyurethane, polysilicone, poly(ethylene-co-vinyl acetate), polyvinyl alcohol, and derivatives and copolymers thereof.

29. The device of claim 1, wherein the polymer is bioerodible.

30. The device of claim 29, wherein the bioerodible polymer is selected from polyanhydride, polylactic acid, polyglycolic acid, polyorthoester, polyalkylcyanoacrylate and derivatives and copolymers thereof.

31. The device of claim 1, wherein the substrate is a surgical implement selected from a screw, a plate, a washer, a suture, a prosthesis anchor, a tack, a staple, an electrical lead, a valve, a membrane, an anastomosis device, a vertegral disk, a bone pin, a suture anchor, a hemostatic barrier, a clamp, a clip, a vascular implant, a tissue adhesive or sealant, a tissue scaffold, a bone substitute, an intraluminal device and a vascular support.

32. The device of claim 1, selected from the group consisting of catheters, implantable vascular access ports, blood storage bags, blood tubing, central venous catheters, arterial catheters, vascular grafts, intraaortic balloon pumps, heart valves, cardiovascular sutures, artificial hearts, a pacemaker, ventricular assist pumps, extracorporeal devices, blood filters, hemodialysis units, hemoperfusion units, plasmapheresis units, filters adapted for deployment in a blood vessel, intraocular lenses, shunts for hydrocephalus, dialysis grafts, colostomy bag attachment devices, ear drainage tubes, leads for pace makers and implantable defibrillators, and osteointegrated orthopedic devices.

33. The device of claim 1, which is a vascular stent.

34. The device of claim 33, which is an expandable stem, end said coating is flexible to accommodate compressed and expanded states of said expandable stent.

35. The device of claim 1, wherein the weight of the coating attributable to the drug is in the range of about 0.05 mg to about 10 mg of drug per cm$^2$ of the surface coated with said polymer matrix.

36. The device of claim 1, wherein the coating has a thickness is in the range of 5 micrometers to 100 micrometers.

37. The device of claim 1, wherein drug is present in an amount between 5% and 70% by weight of the coating.

38. A stent having at least a portion which is insertable or implantable into the body of a patient, wherein the portion has a surface which is adapted for exposure to body tissue and wherein at least a part of the surface is covered with a coating for releasing at least one biologically active material, the coating comprising a polymer matrix having a low solubility prodrug dispersed therein, wherein said low solubility prodrug is represented by the general formula A-L-B, in which A represents a drug moiety having a therapeutically active form for producing a clinical response in a patient;

L represents a covalent linker linking A and B to form a prodrug, said linker being cleaved under physiological conditions to generate said therapeutically active form of A; and B represents a moiety which, when linked to A, results in the prodrug having a lower solubility than the therapeutically active form of A.

* * * * *

UNITED STATES PATENT AND TRADEMARK OFFICE
CERTIFICATE OF CORRECTION

PATENT NO. : 7,279,175 B2 Page 1 of 1
APPLICATION NO. : 10/245840
DATED : October 9, 2007
INVENTOR(S) : Chen et al.

It is certified that error appears in the above-identified patent and that said Letters Patent is hereby corrected as shown below:

In the claims

Column 26, line 51, change "N-pbosphonoacetyl" to --N-phosphonoacetyl--;

Column 28, line 17, change "stern" to --stent--;

Column 28, line 18, change "end" to --and--.

Signed and Sealed this

Fourth Day of March, 2008

JON W. DUDAS
*Director of the United States Patent and Trademark Office*